United States Patent
Yamashita

(10) Patent No.: US 10,265,020 B2
(45) Date of Patent: Apr. 23, 2019

(54) BIOLOGICAL INFORMATION MEASURING MODULE AND BIOLOGICAL INFORMATION MEASURING DEVICE

(71) Applicant: Seiko Epson Corporation, Tokyo (JP)

(72) Inventor: Hideto Yamashita, Suwa (JP)

(73) Assignee: Seiko Epson Corporation, Tokyo (JP)

(*) Notice: Subject to any disclaimer, the term of this patent is extended or adjusted under 35 U.S.C. 154(b) by 695 days.

(21) Appl. No.: 14/982,025

(22) Filed: Dec. 29, 2015

(65) Prior Publication Data
US 2016/0192879 A1 Jul. 7, 2016

(30) Foreign Application Priority Data
Jan. 5, 2015 (JP) ................. 2015-000114

(51) Int. Cl.
*A61B 5/00* (2006.01)
*A61B 5/024* (2006.01)

(52) U.S. Cl.
CPC .......... *A61B 5/681* (2013.01); *A61B 5/02416* (2013.01); *A61B 5/02427* (2013.01); *A61B 5/02438* (2013.01); *A61B 5/721* (2013.01); *A61B 2560/0412* (2013.01)

(58) Field of Classification Search
None
See application file for complete search history.

(56) References Cited

U.S. PATENT DOCUMENTS

| 2011/0166462 A1* | 7/2011 | Iijima ................ A61B 5/02433 600/500 |
| 2014/0275949 A1 | 9/2014 | Takahashi et al. |
| 2014/0276149 A1* | 9/2014 | Takahashi .......... A61B 5/02438 600/503 |

FOREIGN PATENT DOCUMENTS

| JP | 2000-254105 A | 9/2000 |
| JP | 2014-180290 A | 9/2014 |
| JP | 2014-180291 A | 9/2014 |
| WO | WO-2014-091424 A2 | 6/2014 |

* cited by examiner

*Primary Examiner* — Joel F Brutus
(74) *Attorney, Agent, or Firm* — ALG Intellectual Property, LLC

(57) ABSTRACT

A biological information measuring device includes a sensor unit as a biological information measuring module. The sensor unit includes a substrate as a support portion that has a support surface and supports a light receiving portion and a second wall portion as a frame on the support surface. Assuming that the width of the second wall portion is L, a difference Δh between a height h from the support surface to the top surface of the light receiving portion and a height H from the support surface to the top surface of the second wall portion is expressed by Expression (1):

$$\frac{5}{384} \times 0.016 \times L^4 \le \Delta h \le \frac{5}{384} \times 0.039 \times L^4. \quad (1)$$

20 Claims, 22 Drawing Sheets

<TABLE 1>

| DISTANCE L [mm] | HEIGHT DIFFERENCE Δh [mm] | a | EVALUATION RESULT |
|---|---|---|---|
| 9.71 | 1.205 | 0.0104 | × |
| 9.68 | 1.254 | 0.0110 | × |
| 9.66 | 1.302 | 0.0115 | × |
| 9.63 | 1.351 | 0.0121 | × |
| 9.61 | 1.399 | 0.0126 | × |
| 9.58 | 1.448 | 0.0132 | × |

<TABLE 2>

| DISTANCE L [mm] | HEIGHT DIFFERENCE Δh [mm] | a | EVALUATION RESULT |
|---|---|---|---|
| 7.99 | 0.520 | 0.0098 | × |
| 7.97 | 0.568 | 0.0108 | × |
| 7.94 | 0.617 | 0.0119 | × |
| 7.92 | 0.665 | 0.0130 | × |
| 7.89 | 0.713 | 0.0141 | △ |
| 7.87 | 0.762 | 0.0153 | ○ |
| 7.84 | 0.810 | 0.0165 | ○ |
| 7.82 | 0.859 | 0.0176 | ○ |
| 7.79 | 0.907 | 0.0189 | ○ |
| 7.77 | 0.955 | 0.0201 | ◎ |
| 7.74 | 1.004 | 0.0215 | ◎ |
| 7.72 | 1.052 | 0.0227 | ◎ |
| 7.69 | 1.101 | 0.0242 | ◎ |
| 7.67 | 1.149 | 0.0255 | ○ |
| 7.64 | 1.198 | 0.0270 | ○ |
| 7.62 | 1.246 | 0.0284 | ○ |
| 7.59 | 1.294 | 0.0299 | ○ |
| 7.57 | 1.343 | 0.0314 | ○ |
| 7.54 | 1.391 | 0.0331 | ○ |
| 7.52 | 1.440 | 0.0346 | ○ |
| 7.49 | 1.488 | 0.0363 | ○ |
| 7.47 | 1.536 | 0.0379 | ○ |
| 7.44 | 1.585 | 0.0397 | ○ |
| 7.42 | 1.633 | 0.0414 | △ |
| 7.39 | 1.682 | 0.0433 | △ |
| 7.37 | 1.730 | 0.0450 | △ |
| 7.34 | 1.779 | 0.0471 | △ |
| 7.32 | 1.827 | 0.0489 | × |
| 7.29 | 1.875 | 0.0510 | × |
| 7.27 | 1.924 | 0.0529 | × |
| 7.24 | 1.972 | 0.0551 | × |

<TABLE 3>

| DISTANCE L [mm] | HEIGHT DIFFERENCE Δh [mm] | a | EVALUATION RESULT |
|---|---|---|---|
| 6.18 | 0.028 | 0.0015 | × |
| 6.16 | 0.076 | 0.0041 | × |
| 6.13 | 0.125 | 0.0068 | × |
| 6.11 | 0.173 | 0.0095 | × |
| 6.08 | 0.221 | 0.0124 | △ |
| 6.06 | 0.270 | 0.0154 | ○ |
| 6.03 | 0.318 | 0.0185 | ○ |
| 6.01 | 0.367 | 0.0216 | ◎ |
| 5.98 | 0.415 | 0.0249 | ◎ |
| 5.96 | 0.463 | 0.0282 | ◎ |
| 5.93 | 0.512 | 0.0318 | ○ |
| 5.91 | 0.560 | 0.0353 | ○ |
| 5.88 | 0.609 | 0.0391 | ○ |
| 5.86 | 0.657 | 0.0428 | △ |
| 5.83 | 0.705 | 0.0469 | × |
| 5.81 | 0.754 | 0.0508 | × |
| 5.78 | 0.802 | 0.0552 | × |
| 5.76 | 0.851 | 0.0594 | × |
| 5.73 | 0.899 | 0.0640 | × |
| 5.71 | 0.948 | 0.0685 | × |

FIG. 7

<TABLE 4>

| DISTANCE L [mm] | HEIGHT DIFFERENCE Δh [mm] | a | EVALUATION RESULT |
|---|---|---|---|
| 4.12 | 0.020 | 0.0053 | × |
| 4.11 | 0.044 | 0.0118 | △ |
| 4.10 | 0.068 | 0.0185 | ◎ |
| 4.08 | 0.092 | 0.0255 | ◎ |
| 4.07 | 0.117 | 0.0327 | ◎ |
| 4.06 | 0.141 | 0.0399 | ○ |
| 4.05 | 0.165 | 0.0471 | × |
| 4.02 | 0.213 | 0.0626 | × |
| 4.00 | 0.262 | 0.0786 | × |

<TABLE 5>

| DISTANCE L [mm] | HEIGHT DIFFERENCE Δh [mm] | a | EVALUATION RESULT |
|---|---|---|---|
| 3.10 | 0.004 | 0.0033 | × |
| 3.09 | 0.016 | 0.0135 | ○ |
| 3.08 | 0.028 | 0.0239 | ◎ |
| 3.08 | 0.040 | 0.0341 | ○ |
| 3.07 | 0.064 | 0.0553 | △ |
| 3.05 | 0.088 | 0.0781 | △ |
| 3.05 | 0.095 | 0.0843 | △ |
| 3.04 | 0.111 | 0.0998 | × |
| 3.03 | 0.126 | 0.1148 | × |

<TABLE 6>

| DISTANCE L [mm] | HEIGHT DIFFERENCE Δh [mm] | a | EVALUATION RESULT |
|---|---|---|---|
| 2.07 | 0.000 | 0.0000 | × |
| 2.06 | 0.012 | 0.0512 | ○ |
| 2.05 | 0.024 | 0.1044 | ○ |
| 2.05 | 0.036 | 0.1565 | △ |
| 2.04 | 0.048 | 0.2129 | △ |
| 2.03 | 0.060 | 0.2713 | × |
| 2.03 | 0.072 | 0.3256 | × |
| 2.02 | 0.084 | 0.3875 | × |
| 2.02 | 0.097 | 0.4474 | × |

FIG. 8

BIOLOGICAL INFORMATION MEASURING MODULE AND BIOLOGICAL INFORMATION MEASURING DEVICE

CROSS-REFERENCES TO RELATED APPLICATIONS

This application claims priority to Japanese Patent Application No. 2015-000114, filed Jan. 5, 2015, the entirety of which is herein incorporated by reference.

BACKGROUND

1. Technical Field

The present invention relates to a biological information measuring module and a biological information measuring device including a biological information measuring module.

2. Related Art

A measuring device that is worn on the wrist using a band or the like to measure biological information, such as a pulse wave of the wearer, or a watch type electronic device having a biological information measuring function is known. For example, JP-A-2000-254105 discloses a wrist-worn measuring device that is worn on the arm (wrist) of the wearer (subject) and that includes a biological information measuring module for measuring biological information, such as a pulse wave, using an optical pulse wave detection sensor.

In such devices (the measuring device and the electronic device), biological information, such as a pulse wave, is obtained by optically measuring the blood flow of the skin surface, which is a measurement target, and signaling the measurement result. Accordingly, a light emitting portion, a light receiving portion, and the peripheral configuration, for example, the setting of the distance between the skin surface, which is a measurement target, and the light receiving portion becomes a very important factor in order to obtain accurate information.

For example, when such devices (the measuring device and the electronic device) are used for sport applications, portability, miniaturization, and weight reduction are very important points to ensure that the mounted devices do not affect the performance of the wearer (subject). Even when such devices (the measuring device and the electronic device) are used for medical and health applications, for example, consideration not to put a load on the patient or the subject is needed. Also in this case, portability, miniaturization, and weight reduction are very important points. Thus, in the device that is worn on a part, such as the wrist, to obtain biological information, portability, miniaturization, and weight reduction are severely required.

In the wrist-worn measuring device disclosed in JP-A-2000-254105, however, there is no detailed description of the light emitting portion, the light receiving portion, and the peripheral configuration, for example, the setting of the distance between the skin surface, which is a measurement target, and the light receiving portion. In addition, reference to problems related to the configuration for obtaining the accurate information has not been made.

SUMMARY

An advantage of some aspects of the invention is to solve at least a part of the problems described above, and the invention can be implemented as the following forms or application examples.

Application Example 1

A biological information measuring module according to this application example includes: a light receiving portion that receives light having passed through a target; a frame that surrounds the light receiving portion; and a support portion that has a support surface and supports the light receiving portion and the frame on the support surface. Assuming that a width of the frame is L, a difference $\Delta h$ between a height from the support surface to a top surface of the light receiving portion on an opposite side of the support surface and a height from the support surface to a top surface of the frame on an opposite side of the support surface is expressed by Expression (1).

$$\frac{5}{384} \times 0.016 \times L^4 \le \Delta h \le \frac{5}{384} \times 0.039 \times L^4 \quad (1)$$

In the biological information measuring module, in order to accurately receive the light having passed through the measurement target in the light receiving portion and to acquire accurate information, the distance (gap) from the target to the light receiving portion is important. Therefore, a configuration in which the distance (gap) can be easily set to a predetermined value is required.

According to this application example, by setting the difference $\Delta h$ between the height from the support surface to the top surface of the light receiving portion and the height from the support surface to the top surface of the frame surrounding the light receiving portion within the range expressed by the above Expression (1), it is possible to obtain the distance between the target and the light receiving portion at which the light receiving portion can accurately receive the light having passed through the measurement target. Therefore, it is possible to accurately acquire biological information, such as a pulse wave.

Application Example 2

In the biological information measuring module described in the above application example, it is preferable that the difference $\Delta h$ is expressed by Expression (2).

$$\frac{5}{384} \times 0.020 \times L^4 \le \Delta h \le \frac{5}{384} \times 0.025 \times L^4 \quad (2)$$

According to this application example, by setting the difference $\Delta h$ between the height from the support surface to the top surface of the light receiving portion and the height from the support surface to the top surface of the frame surrounding the light receiving portion within the range expressed by the above Expression (2), it is possible to obtain the S/N ratio of 1 or more. Therefore, it is possible to acquire the more accurate biological information.

Application Example 3

In the biological information measuring module described in the above application example, it is preferable that the width L is 3.0 mm$\le$L<4.5 mm.

A measurement target of the biological information measuring module, for example, a blood vessel to be noted is located about 0.3 mm under the skin. Therefore, in order that the light receiving portion accurately receives the light reflected from the target, it is advantageous that the width L of the frame is large. However, if the width L of the frame is increased, the area of the biological information measuring module in the planar direction is increased. If the width L of the frame exceeds 4.5 mm, portability becomes worse. For example, there is discomfort at the time of wearing. On the other hand, if the width L of the frame is too small, it is difficult for the light receiving portion to accurately receive the light reflected from the target. If the width L of the frame is not 0.3 mm or more, the light receiving portion cannot accurately receive the light reflected from the blood vessel.

According to this application example, by setting the width L of the frame within the range of 0.3 mm≤L<4.5 mm, it is possible to provide the biological information measuring module capable of acquiring the accurate biological information without having an adverse effect on portability in daily life.

Application Example 4

In the biological information measuring module described in the above application example, it is preferable that the width L is 4.0 mm≤L<4.5 mm.

According to this application example, since it is possible to make the biological information measuring module smaller, the movement of the biological information measuring module is unlikely to occur even if any impact due to hard exercise or the like is given to the biological information measuring module mounted on the target. Therefore, it is possible to accurately measure biological information and to further improve portability.

Application Example 5

In the biological information measuring module described in the above application example, it is preferable that the frame has a rectangular shape in plan view and the width L is a width of the frame in a short side direction of the rectangular shape.

According to this application example, it is possible to define the width of the frame in the short side direction of the rectangular shape, which is dominant with respect to the deformation of the target. Therefore, it is possible to provide the biological information measuring module capable of acquiring the accurate biological information without having an adverse effect on portability.

Application Example 6

In the biological information measuring module described in the above application example, it is preferable that the height from the support surface to a top surface of the frame on the opposite side of the support surface is larger by Δh than the height from the support surface to the top surface of the light receiving portion on the opposite side of the support surface.

According to this application example, it is possible to easily and accurately obtain the distance (gap) at which the light receiving portion can accurately receive the light having passed through the target.

Application Example 7

In the biological information measuring module described in the above application example, it is preferable that a light emitting portion that emits light to the target is provided and the light emitting portion is supported on the support surface of the support portion.

According to this application example, since the light emitting portion, the light receiving portion, and the frame are supported by the support portion, it is possible to achieve space saving. Therefore, it is possible to realize a compact biological information measuring module.

Application Example 8

In the biological information measuring module described in the above application example, it is preferable that at least a part of the frame is disposed between the light receiving portion and the light emitting portion.

According to this application example, at least a part of the frame disposed between the light receiving portion and the light emitting portion can prevent light emitted from the light emitting portion from being directly incident on the light receiving portion. Therefore, since light with few noise components can be incident on the light receiving portion, it is possible to further improve the measurement accuracy of the biological information measuring module.

Application Example 9

In the biological information measuring module described in the above application example, it is preferable that the width L is a width of the frame in a direction in which the light receiving portion and the light emitting portion are connected to each other.

According to this application example, the width L of the frame is the width of the frame in a direction in which the light receiving portion and the light emitting portion are connected to each other. Thus, by arranging the light receiving portion, the light emitting portion, and the frame, the relationship between the positions of the light receiving portion and the light emitting portion and the width of the frame is defined. Therefore, it is possible to obtain the more accurate biological information.

Application Example 10

In the biological information measuring module described in the above application example, it is preferable that a control unit is further provided and the support portion includes a connection terminal that electrically connects the light receiving portion and the control unit to each other.

According to this application example, the connection terminal provided in the support portion enables a compact connection between the support portion and the control unit.

Application Example 11

In the biological information measuring module described in the above application example, it is preferable that the support portion includes a through hole that connects the support surface and aback surface of the support portion, which are front and back surfaces of the support portion, to each other and the connection terminal is provided on the back surface of the support portion so as to be connected to the through hole.

According to this application example, since the support portion and the control unit can be connected to each other through the connection terminal that is provided on the back surface of the support portion so as to be connected to the through hole, for example, it is possible to arrange the light receiving portion, the light emitting portion, and the frame on the support surface side of the support portion and to arrange the control unit on the back surface side. Through such an arrangement, it is possible to realize space saving and miniaturization of the biological information measuring module.

Application Example 12

In the biological information measuring module described in the above application example, it is preferable that a thickness of the support portion is larger than a thickness of a base portion of the control unit.

According to this application example, since the base portion of the control unit is supported by the strong support portion, it is possible to increase the strength of the biological information measuring module.

Application Example 13

A biological information measuring device according to this application example includes the biological information measuring module according to any of the above application examples.

According to this application example, the biological information measuring module, which can perform detection (measurement) more accurately and which is small and is excellent in portability, is provided. Therefore, it is possible to provide the biological information measuring device that can detect biological information stably even at the time of exercise or the like and that is small and is excellent in portability (wearability).

BRIEF DESCRIPTION OF THE DRAWINGS

The invention will be described with reference to the accompanying drawings, wherein like numbers reference like elements.

FIG. 5A is a front sectional view and FIG. 5B is a plan view seen from the line A-A in FIG. 5A.

FIG. 6A is a front sectional view of FIG. 5B and FIG. 6B is a partially enlarged view (front sectional view) of FIG. 6A.

FIG. 7 is Tables 1 to 3 showing the evaluation result of the relationship between the width of a frame and the height difference between a light receiving portion and the frame.

FIG. 8 is Tables 4 to 6 showing the evaluation result of the relationship between the width of a frame and the height difference between a light receiving portion and the frame.

FIG. 11A is a plan view seen from the same direction as the line A-A in FIG. 5A and FIG. 11B is a front sectional view of FIG. 11A.

DESCRIPTION OF EXEMPLARY EMBODIMENTS

Hereinafter, the present embodiment will be described. The present embodiment described below is not intended to limit the content of the invention described in the appended claims. In addition, all components described in the present embodiment are not necessarily essential components of the invention.

First Embodiment

Figure 1A:
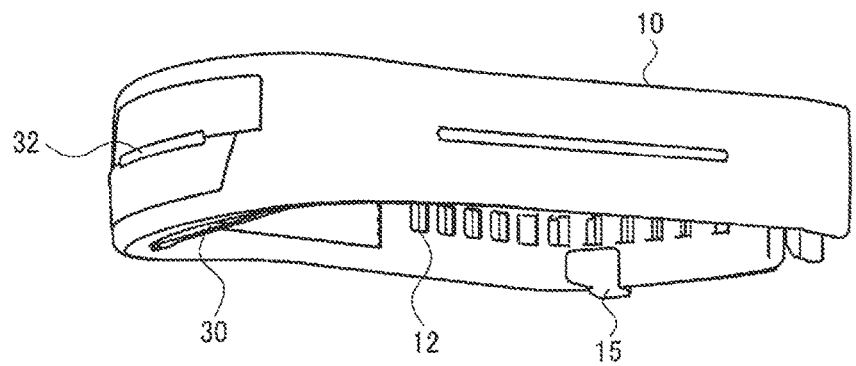
FIGS. 1A and 1B are perspective views showing the outer appearance of a biological information measuring device according to a first embodiment.
Figure 1B:
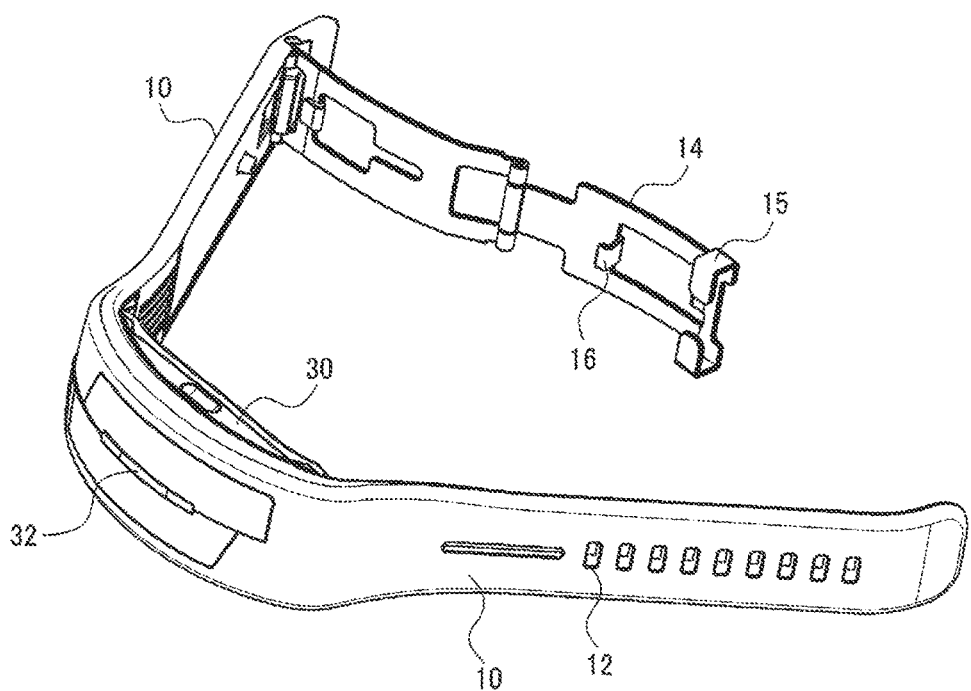
Figure 2:
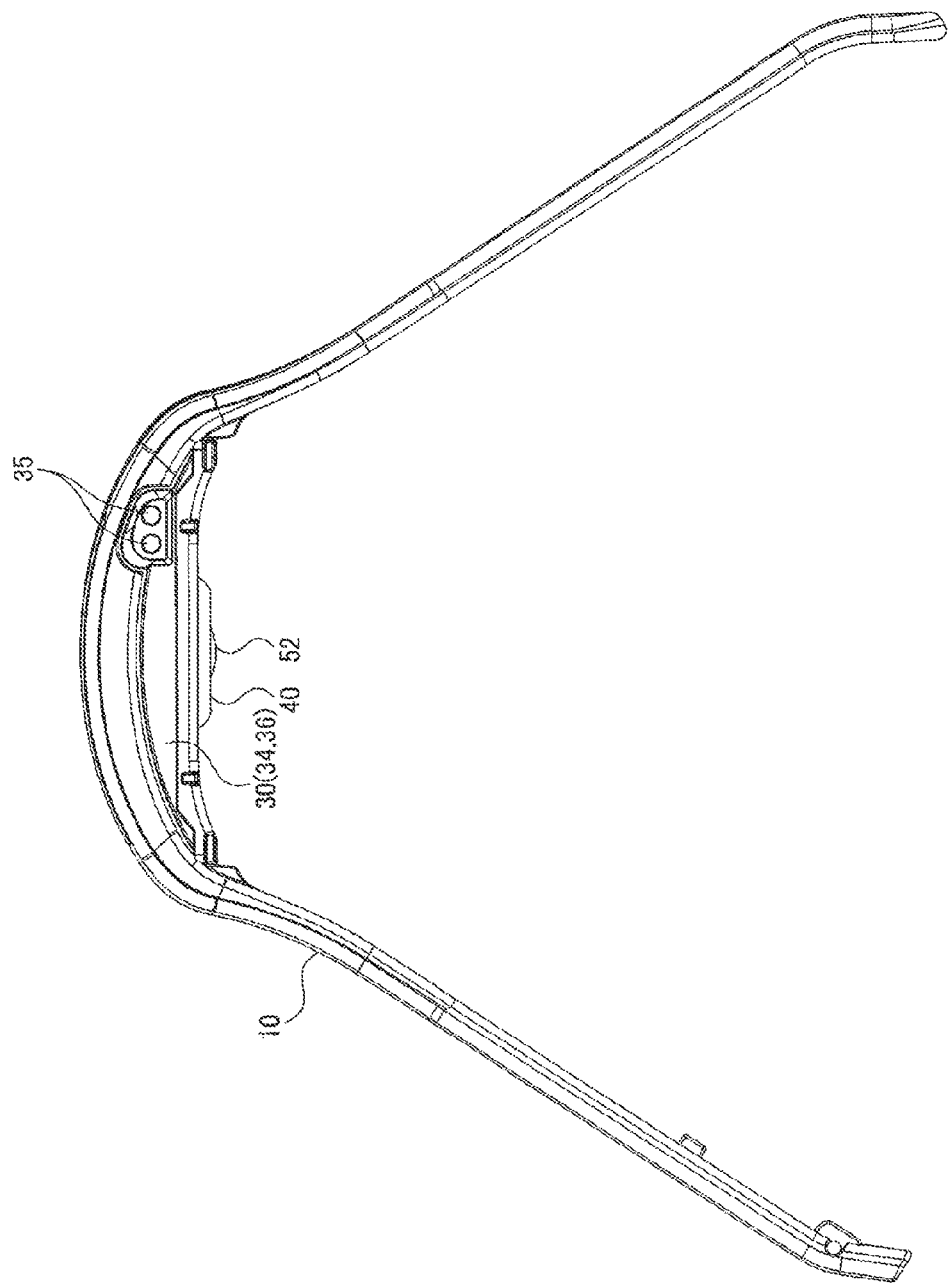
FIG. 2 is a side view showing the outer appearance of the biological information measuring device of the first embodiment.

1. Example of the Overall Configuration of a Biological Information Measuring Device FIGS. 1A, 1B, and 2 are external views showing the schematic configuration of a biological information measuring device (biological information detecting device) according to a first embodiment. FIG. 1A is a diagram when the biological information measuring device is viewed from the front direction side, FIG. 1B is a diagram when the biological information measuring device is viewed from the obliquely upward side in FIG. 1A, and FIG. 2 is a diagram when the biological information measuring device is viewed from the side direction side.

Figure 4:
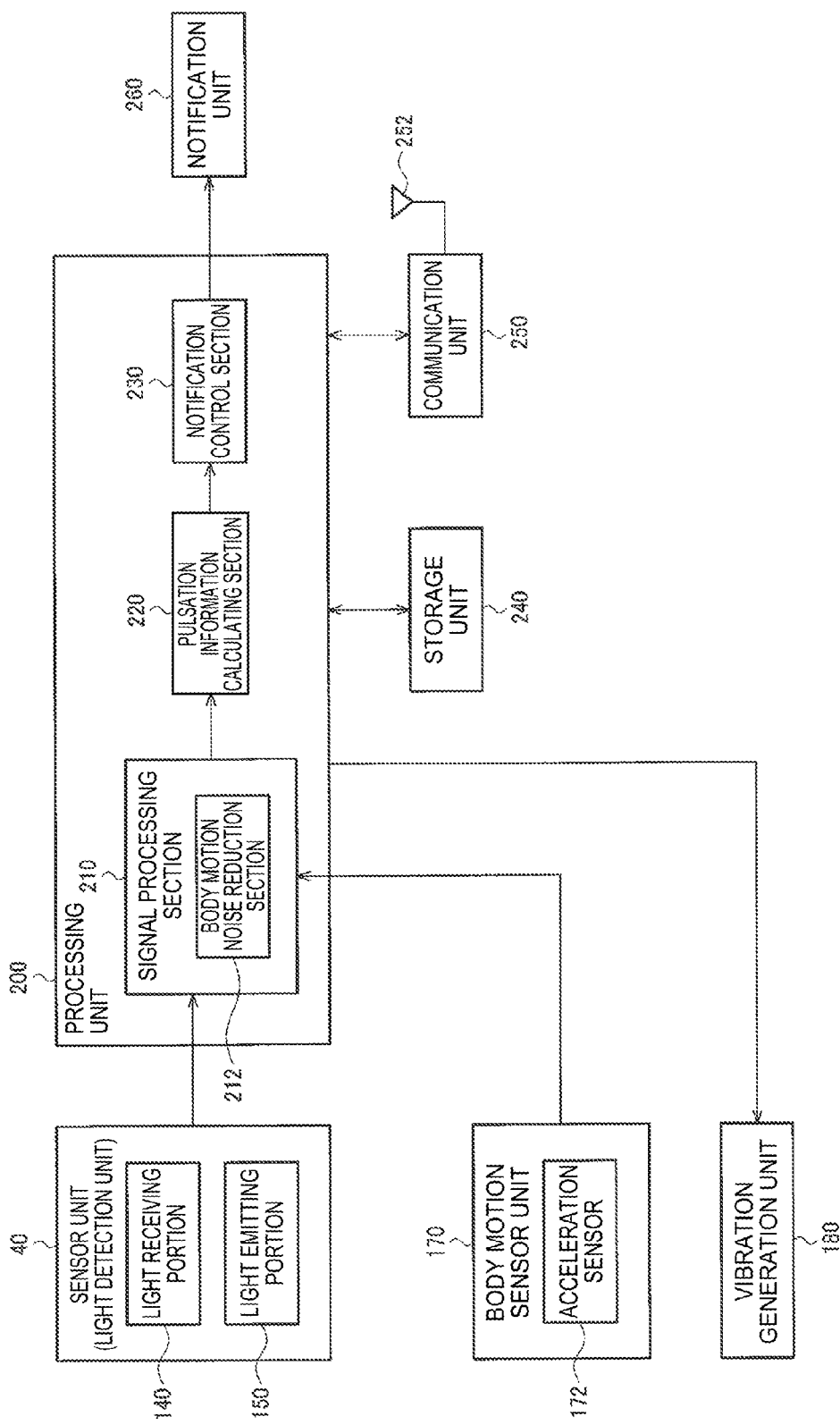
FIG. 4 is a functional block diagram of the biological information measuring device.

As shown in FIGS. 1A, 1B, and 2, the biological information measuring device of the present embodiment includes a band unit 10, a case unit 30, and a sensor unit 40 as a biological information measuring module. The case unit 30 is attached to the band unit 10. The sensor unit 40 is provided in the case unit 30. In addition, as shown in FIG. 4 to be described later, the biological information measuring device includes a processing unit 200. The processing unit 200 is provided in the case unit 30, and detects biological information based on a detection signal from the sensor unit 40. The biological information measuring device of the present embodiment is not limited to the configuration shown in FIGS. 1A, 1B, and 2, and various modifications can be made. For example, some of the components may be omitted or may be replaced with other components, or other components may be added.

As will be described later with reference to FIG. 5A, the sensor unit 40 as a biological information measuring module is configured to include a substrate 160, a light emitting portion 150, a light receiving portion 140, first and second wall portions 71 and 72 as frames including a wall portion 70, a light detection unit including a diaphragm portion 80 (80a, 80b), and other members. In the example shown in FIG. 5A, other members are a protruding portion 52 realized by a light-transmissive member 50, a groove 54, a recess 56, a pressure suppressing portion 58, and the like. However, modifications can also be made in which the light detection unit according to the present embodiment includes these members, that is, the entire sensor unit 40 corresponds to the light detection unit.

FIGS. 1A, 1B, and 2 will be referred to again. The band unit 10 is wound around the wrist of a wearer (hereinafter, referred to as a user) so that the biological information measuring device is worn thereon. The band unit 10 includes a band hole 12 and a buckle portion 14. The buckle portion 14 includes a band insertion portion 15 and a protruding portion 16. The user wears the biological information measuring device on the wrist by inserting one end of the band unit 10 into the band insertion portion 15 of the buckle portion 14 and inserting the protruding portion 16 of the buckle portion 14 into the band hole 12 of the band unit 10. In this case, depending on to which band hole 12 the protruding portion 16 is inserted, the magnitude of the pressure on the sensor unit (pressure against the wrist surface), which will be described later, is adjusted.

The case unit 30 corresponds to the main body of the biological information measuring device. Various components of the biological information measuring device, such as the sensor unit 40 and the processing unit 200 (refer to FIG. 4), are provided in the case unit 30. That is, the case unit 30 is a housing in which these components are housed. The case unit 30 includes, for example, a top case 34 located on the opposite side of the wrist and a bottom case 36 located on the wrist side. In addition, the case unit 30 may not be divided into the top case 34 and the bottom case 36.

A light emitting window 32 is provided in the case unit 30. The light emitting window 32 is formed by a light-transmissive member. In addition, a light emitting portion (LED; a light emitting portion for notification that is different from the light emitting portion 150 of the light detection unit) mounted on a flexible substrate is provided in the case unit 30, and light from the light emitting portion is emitted to the outside of the case unit 30 through the light emitting window 32.

As shown in FIG. 2, a terminal portion 35 is provided in the case unit 30. When the biological information measuring device is mounted on a cradle (not shown), a terminal portion of the cradle and the terminal portion 35 of the case unit 30 are electrically connected to each other. Therefore, a secondary battery (battery) provided in the case unit 30 can be charged.

The sensor unit 40 as a biological information measuring module detects biological information, for example, the pulse wave of the subject. For example, the sensor unit 40 includes the light receiving portion 140 and the light emitting portion 150, as shown in FIGS. 4 and 5 to be described later. In addition, the sensor unit 40 is formed by the light-transmissive member 50, and includes the protruding portion 52 that is in contact with the skin surface of the subject to apply pressure to the skin surface. In a state in which the protruding portion 52 applies pressure to the skin surface as described above, the light emitting portion 150 emits light, the light receiving portion 140 receives light reflected by the subject (blood vessel), and the light receiving result is output to the processing unit 200 as a detection signal. Then, the processing unit 200 detects biological information, such as a pulse wave, based on the detection signal from the sensor unit 40. In addition, biological information to be detected by the biological information measuring device of the present embodiment is not limited to the pulse wave (pulse rate), and the biological information measuring device may detect biological information (for example, blood oxygen saturation, body temperature, or a heart rate) other than the pulse wave.

Figure 3:
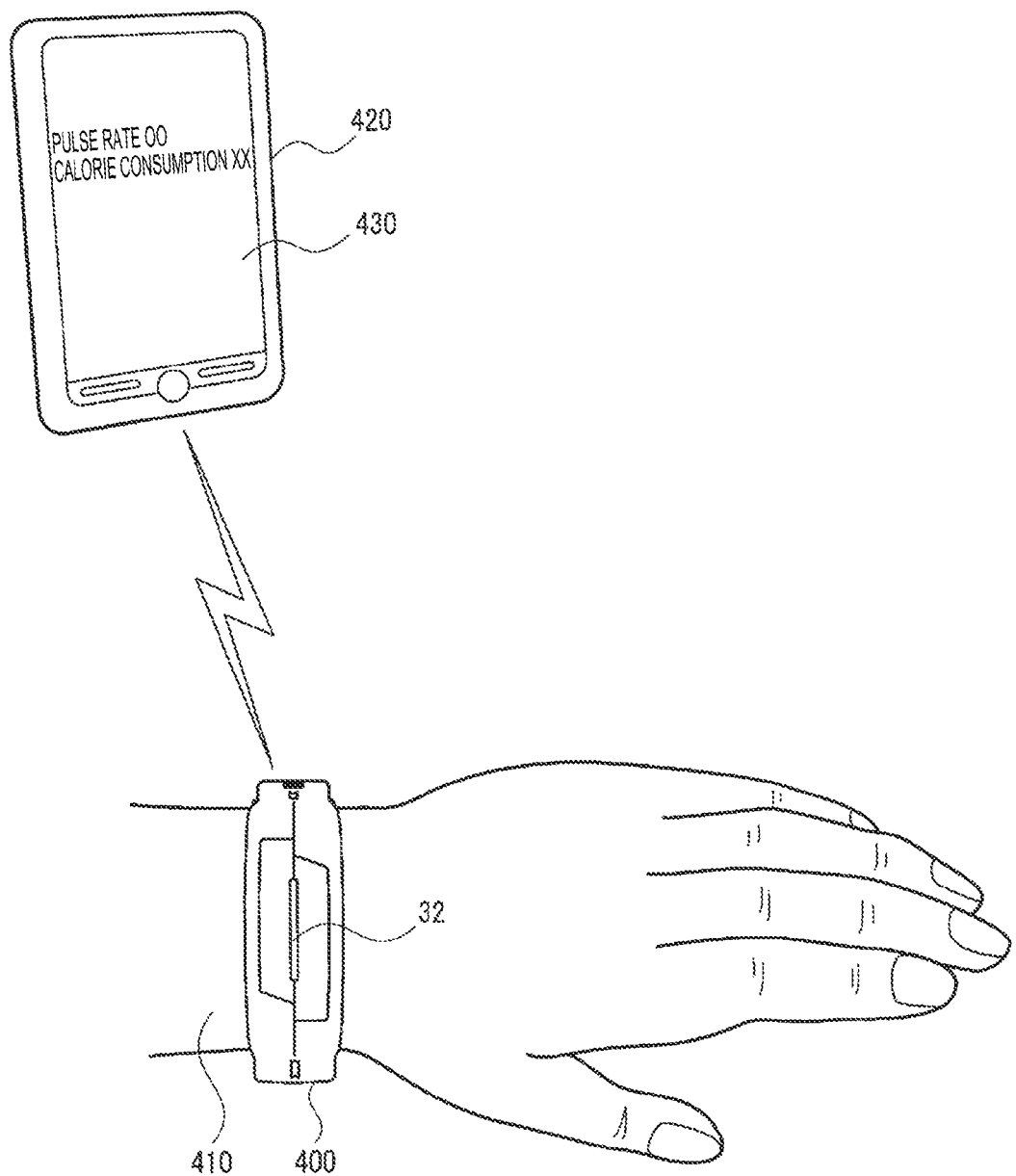
FIG. 3 is a diagram for explaining the mounting of the biological information measuring device and communication with a terminal device.

FIG. 3 is an explanatory diagram schematically showing the mounting of a biological information measuring device 400 and communication with a terminal device 420. As shown in FIG. 3, a user who is a subject wears the biological information measuring device 400 on a wrist 410 as a watch. As shown in FIG. 2, the sensor unit 40 is provided on the surface of the case unit 30 on the subject side. Accordingly, when the biological information measuring device 400 is worn, the protruding portion 52 of the sensor unit 40 is in contact with the skin surface of the wrist 410 to apply pressure to the skin surface. In this state, the light emitting portion 150 of the sensor unit 40 emits light, and the light receiving portion 140 receives the reflected light. As a result, biological information, such as a pulse wave, is detected.

The biological information measuring device 400 and the terminal device 420 are communicably connected to each other, so that the transmission and reception of data therebetween are possible. For example, the terminal device 420 is a portable communication terminal, such as a smartphone, a mobile phone, and a future phone. Alternatively, the terminal device 420 may be an information processing terminal, such as a tablet computer. As a communication connection between the biological information measuring device 400 and the terminal device 420, for example, near field communication, such as Bluetooth (registered trademark), can be adopted. Thus, since the biological information measuring device 400 and the terminal device 420 are communicably connected to each other, various kinds of information, such as a pulse rate or calorie consumption, can be displayed on a display unit 430 (LCD or the like) of the terminal device 420. That is, various kinds of information calculated based on the detection signal of the sensor unit 40 can be displayed. In addition, arithmetic processing of information, such as a pulse rate or calorie consumption, may be performed in the biological information measuring device 400, or at least a part of the arithmetic processing may be performed in the terminal device 420.

The light emitting window 32 is provided in the biological information measuring device 400, so that the user is notified of various kinds of information through the emission (lighting or blinking) of a light emitter for notification (not shown). For example, in information such as calorie consumption, when the user goes into the fat burning zone or comes out from the fat burning zone, the user is notified of this by the emission of the light emitter through the light emitting window 32. When an e-mail or the like is received by the terminal device 420, this is notified to the biological information measuring device 400 from the terminal device 420. Then, the light emitter of the biological information measuring device 400 emits light, so that the user is notified of the reception of the e-mail or the like.

Thus, in the example shown in FIG. 3, a display unit, such as an LCD, is not provided in the biological information measuring device 400, and information that needs to be notified in letters, numbers, or the like is displayed on the display unit 430 of the terminal device 420. Thus, in the example shown in FIG. 3, the miniaturization of the biological information measuring device 400 is realized by notifying the user of the minimum necessary information through the emission of the light emitter without providing a display unit, such as an LCD. In addition, it is also possible to improve the appearance of the biological information measuring device 400 by providing no display unit in the biological information measuring device 400.

FIG. 4 shows a functional block diagram of the biological information measuring device of the present embodiment. The biological information measuring device shown in FIG. 4 includes the sensor unit 40 as a biological information measuring module, a body motion sensor unit 170, a vibration generation unit 180, the processing unit 200, a storage unit 240, a communication unit 250, an antenna 252, and a notification unit 260. The biological information measuring device of the present embodiment is not limited to the configuration shown in FIG. 4, and various modifications can be made. For example, some of the components may be omitted or may be replaced with other components, or other components may be added.

The sensor unit 40 as a biological information measuring module detects biological information, such as a pulse wave, and includes the light receiving portion 140 and the light emitting portion 150. A pulse wave sensor (photoelectric sensor) is realized by the light receiving portion 140, the light emitting portion 150, and the like. The sensor unit 40 outputs a signal detected by the pulse wave sensor as a pulse wave detection signal.

The body motion sensor unit 170 outputs a body motion detection signal, which is a signal that changes according to the body motion, based on the sensor information of various sensors. The body motion sensor unit 170 includes, for example, an acceleration sensor 172 as a body motion sensor. In addition, the body motion sensor unit 170 may include a pressure sensor, a gyro sensor, or the like as a body motion sensor.

The processing unit 200 performs various kinds of signal processing or control processing, for example, with the storage unit 240 as a work region. For example, the processing unit 200 can be realized by a processor, such as a CPU, or a logic circuit, such as an ASIC. The processing unit 200 includes a signal processing section 210, a pulsation information calculating section 220, and a notification control section 230.

The signal processing section 210 performs various kinds of signal processing (filtering processing or the like). For example, the signal processing section 210 performs signal processing on the pulse wave detection signal from the sensor unit 40, the body motion detection signal from the body motion sensor unit 170, and the like. For example, the signal processing section 210 includes a body motion noise reduction section 212. The body motion noise reduction section 212 performs processing for reducing (removing) the body motion noise, which is noise due to body motion, from the pulse wave detection signal based on the body motion detection signal from the body motion sensor unit 170. Specifically, for example, noise reduction processing using an adaptive filter or the like is performed.

The pulsation information calculating section 220 performs arithmetic processing of the pulsation information based on the signal from the signal processing section 210 or the like. For example, the pulsation information is information, such as a pulse rate. Specifically, the pulsation information calculating section 220 acquires a spectrum by performing frequency analysis processing, such as FFT, on the pulse wave detection signal after the noise reduction processing of the body motion noise reduction section 212, and sets a representative frequency in the acquired spectrum as a frequency of the cardiac beat. A value obtained by multiplying the obtained frequency by 60 is a pulse rate (heart rate) that is generally used. The pulsation information is not limited to the pulse rate itself, and may be other various kinds of information (for example, a frequency or a period of the cardiac beat) indicating the pulse rate, for example. In addition, the pulsation information may be information indicating the state of pulsation. For example, the pulsation information may be a value indicating the amount of blood itself.

The notification control section 230 controls the notification unit 260. The notification unit 260 (notification device) notifies the user of various kinds of information under the control of the notification control section 230. As the notification unit 260, for example, alight emitter for notification can be used. In this case, the notification control section 230 controls the lighting, blinking, and the like of the light emitter by controlling the current flowing through the LED. The notification unit 260 may be a display unit, such as an LCD, or a buzzer.

The notification control section 230 controls the vibration generation unit 180. The vibration generation unit 180 notifies the user of various kinds of information by vibration. For example, the vibration generation unit 180 can be realized by a vibration motor (vibrator). The vibration motor generates vibration, for example, by rotating the eccentric weight. Specifically, an eccentric weight is attached to both ends of the driving shaft (rotor shaft), so that the motor itself swing. The vibration of the vibration generation unit 180 is controlled by the notification control section 230. In addition, the vibration generation unit 180 is not limited to such a vibration motor, and various modifications can be made. For example, the vibration generation unit 180 may be realized using a piezoelectric element.

By the vibration generated by the vibration generation unit 180, for example, notification of start-up when the power is turned on, notification of the success of the first pulse wave detection, warning when a state in which a pulse wave cannot be detected continues for a predetermined period of time, notification at the time of movement to the fat burning zone, warning when the battery voltage drops, notification of wake-up alarm, or notification of a call or e-mail from the terminal device, such as a smartphone, becomes possible. These pieces of information may be notified by the light emitting portion for notification, or may be notified by both the vibration generation unit 180 and the light emitting portion.

The communication unit 250 performs processing for communication with the external terminal device 420 as described in FIG. 3. For example, the communication unit 250 performs processing for radio communication according to the specifications of Bluetooth (registered trademark) or the like. Specifically, the communication unit 250 performs processing for receiving the signal from the antenna 252 or processing for transmitting the signal to the antenna 252. The function of the communication unit 250 can be realized by a processor for communication or a logic circuit, such as an ASIC.

2. Example of the Configuration of a Sensor Unit as a Biological Information Measuring Module An example of the detailed configuration of the sensor unit 40 as a biological information measuring module will be described with reference to FIGS. 5A to 8. FIGS. 5A to 6B are diagrams showing Configuration Example 1 of the sensor unit 40. FIG. 5A is a front sectional view, FIG. 5B is a plan view seen from the line A-A in FIG. 5A, FIG. 6A is a front sectional view of FIG. 5B, and FIG. 6B is a partially enlarged view (front sectional view) of FIG. 6A. FIGS. 7 and 8 are Tables 1 to 6 showing the evaluation result of the relationship between the width L of a frame and the height difference Δh between the light receiving portion and the frame.

Configuration Example 1 of the Sensor Unit

First, Configuration Example 1 of the sensor unit 40 will be described with reference to FIGS. 5A to 6B. The sensor unit 40 of Configuration Example 1 includes the light receiving portion 140 and the light emitting portion 150. The light receiving portion 140 and the light emitting portion 150 are aligned with a predetermined gap interposed therebetween, and are mounted on a support surface 160a of the substrate 160 (sensor substrate) as a support portion. The light emitting portion 150 emits light to a target (for example, a subject). Then, the light receiving portion 140 receives light (reflected light, transmitted light, or the like) having passed through the target. For example, when the light emitting portion 150 emits light and the light is reflected by the target (for example, blood vessels), the light receiving portion 140 receives and detects the reflected light. The light receiving portion 140 can be realized by a light receiving element, such as a photodiode. The light emitting portion 150 can be realized by a light emitting element, such as an LED. For example, the light receiving portion 140 can be realized by a PN-junction diode element formed on the semiconductor substrate. In this case, an angle limiting filter for narrowing down the light receiving angle or a wavelength limiting filter (optical filter film) for limiting the wavelength of light incident on the light receiving element may be formed on the diode element.

A dome-shaped lens 151 (in a broad sense, a condensing lens) as a condensing portion provided in the light emitting portion 150 is a lens for condensing light from an LED chip (in a broad sense, a light emitting element chip), which is sealed with resin (sealed with light-transmissive resin), to the light emitting portion 150. That is, in the surface mounting type light emitting portion 150, an LED chip is disposed below the dome-shaped lens 151, and light from the LED chip is condensed by the dome-shaped lens 151 and is emitted to the target. In this manner, since it is possible to increase the intensity of light emitted to the target, it is possible to improve the optical efficiency of the light detection unit. As a result, it is possible to perform more accurate measurement.

For example, when the biological information measuring device is a pulse counter, light emitted from the light emitting portion 150 proceeds along the inside of the subject as a target, and is diffused or scattered in the epidermis, dermis, subcutaneous tissue, and the like. Then, the light reaches a blood vessel (part to be detected) and is reflected. In this case, some of the light beams are absorbed by the blood vessel. In addition, the light absorption rate in a blood vessel changes due to the influence of the pulse, and the amount of reflected light is also changed. Therefore, the light receiving portion 140 receives the reflected light and detects a change in the amount of light, so that it is possible to detect the pulse rate that is biological information and the like.

In such a biological information measuring device, biological information, such as a pulse wave and a pulse, is obtained by optically measuring and signaling the blood flow of the skin surface. Accordingly, in order to improve the accuracy of measurement or portability, it is important to reduce the amount of noise components, such as disturbance light, in the optical path from the light emitting portion 150 to the light receiving portion 140 or to reduce the amount of light that is directly incident on the light receiving portion 140 from the light emitting portion 150 (direct light or the like). From such a point of view, the inventors have provided a light blocking portion, which will be described below, and have studied and verified the size-related relationship of the light blocking portion (wall portion). As a result, the inventors have found the arrangement (configuration) or size relationship of the light blocking portions (wall portions) that are excellent in portability while ensuring the accuracy or stability of measurement.

In this configuration example, the first and second wall portions 71 and 72 as frames surrounding the outer periphery 140b of the light receiving portion 140 and the outer periphery 150b of the light emitting portion 150 are provided in the sensor unit 40. The wall portion 70 as a light blocking portion is included in at least apart of the second wall portion 72 surrounding the light receiving portion 140 that is mounted on the support surface 160a of the substrate 160 as a support portion. The wall portion 70 is provided between the light receiving portion 140 and the light emitting portion 150. The first and second wall portions 71 and 72 as frames hold the skin of the subject as a target on its top surface (upper surface), and forms a desired space on the upper surface of the light receiving portion 140 or the light emitting portion 150. Using the wall portion 70, the first and second wall portions 71 and 72 block light, such as direct light that is directly incident on the light receiving portion 140 from the light emitting portion 150 or disturbance light that is a noise component incident on the light receiving portion 140. Thus, since the wall portion 70 is provided in at least a part of the second wall portion 72, light emitted from the light emitting portion 150 can be prevented from directly reaching (being incident on) the light receiving portion 140. Therefore, since light with few noise components can be incident on the light receiving portion 140, it is possible to further improve the measurement accuracy of the biological information measuring module.

The first and second wall portions 71 and 72 as frames can be formed by sheet metal processing on a metal plate, for example. If the first and second wall portions 71 and 72 are formed by the sheet metal processing on the metal plate, it is possible to easily form the first and second wall portions 71 and 72 having excellent strength with an inexpensive material and to reflect light with the first and second wall portions 71 and 72 that are formed of metal. As a result, it is possible to emit light, which is emitted from the light emitting portion 150, to the subject as a target efficiently or to make light reflected from the subject incident on the light receiving portion 140 efficiently. As materials of the first and second wall portions 71 and 72 other than the metal material, resins (including a natural resin and a synthetic resin), such as rubber, can be mentioned. These materials can be easily obtained at low cost, and the first and second wall portions 71 and 72 can be easily formed of these materials.

In the sensor unit 40, in order to accurately receive light having passed through a measurement target (for example, skin 411 of the subject) in the light receiving portion 140 and acquire the accurate biological information, a distance (distance CL) from the target to the light receiving portion 140 is important. Therefore, a configuration capable of easily setting the distance (distance CL) to a predetermined value is required. Specifically, if the distance (distance CL) from the target to the light receiving portion 140 is too large, a space is generated between the target and the top surface (upper surface) 140c of the light receiving portion 140. As a result, the loss of light is increased by the presence of an air layer existing between the target and the top surface (upper surface) 140c of the light receiving portion 140. On the other hand, if the distance (distance CL) from the target to the light receiving portion 140 is too small, a change in the measurement environment due to the operation of the target or the like or the influence of body motion noise is increased. As a result, light reception in the light receiving portion 140 becomes unstable, or the S/N ratio is reduced.

The inventors have found that the distance (distance CL) from the target to the light receiving portion 140 can be appropriately set by calculating the amount of deformation of the skin 411 to the light receiving portion 140 side based on the following Expression (3) to calculate the amount of bending in the both-ends support beam, i.e., a simple beam whose both ends are open ends. Specifically, assuming that two top surfaces 72b located in a width direction with a width L therebetween in the second wall portion 72 are support portions at both ends, the distance (distance CL) from the target to the light receiving portion 140 can be appropriately set from the correlation between the amount of deformation of the skin 411 to the light receiving portion 140 side and a difference Δh between the height h to the top surface 140c of the light receiving portion 140 and the height H to the top surface 72b of the second wall portion 72.

$$\delta_{max} = \frac{5 \cdot \omega \cdot l^4}{384 \cdot E \cdot I} \quad (3)$$

wherein ω: full load, E: Young's modulus, I: elastic secondary moment, l: distance between support portions More specifically, in Expression (3), the skin 411 of the subject is regarded as a beam across both open ends, and the amount of bending (δmax) of the both-ends support beam (simple beam) when the two top surfaces 72b (width L) in the width direction of the second wall portion 72 are support portions is set to the difference Δh between the height h to the top surface 140c of the light receiving portion 140 and the height H to the top surface 72b of the second wall portion 72. In other words, even if the skin 411 is pressed against the top surface 72b of the second wall portion 72, a distance at which the skin 411 is not in contact with the top surface 140c of the light receiving portion 140 (distance between the top surface 140c of the light receiving portion 140 and the top surface 72b of the second wall portion 72) is calculated.

Here, the full load ω is the pressure at which the skin 411 is pressed against the top surface 72b of the second wall portion 72. Therefore, by appropriately selecting the full load ω from 4 KPa to 12 KPa that is the required pressure and setting the Young's modulus E and the elastic secondary moment I as coefficients for the skin of the subject (human being), ω/EI can be set as a coefficient a. In addition, the distance l between support portions is assumed to be the width (hereinafter, referred to as "width L") of the second wall portion 72 in a direction in which the light receiving portion 140 and the light emitting portion 150 are connected to each other (X-axis direction in the diagram). From these, the difference Δh between the height h to the top surface 140c of the light receiving portion 140 and the height H to the top surface 72b of the second wall portion 72 can be defined by the width L of the second wall portion 72 and the coefficient a. Therefore, the following Expression (1) is obtained. In addition, it has been found that the distance (distance CL), at which the light receiving portion 140 can accurately receive light having passed through the skin 411 of the subject, can be obtained easily and accurately by setting the difference Δh so as to satisfy Expression (1).

According to the above, assuming that the width of the second wall portion 72 in a direction in which the light receiving portion 140 and the light emitting portion 150 are connected to each other (X-axis direction in the diagram) in the sensor unit 40 is the width L, it is preferable that the difference Δh between the height h from the support surface 160a of the substrate 160 to the top surface 140c of the light receiving portion 140 and the height H from the support surface 160a to the top surface 72b of the second wall portion 72 is set within the range expressed by the following Expression (1). In Expression (1), "0.016" and "0.039" are constants corresponding to the coefficient a described above, and are coefficients determined empirically.

$$\frac{5}{384} \times 0.016 \times L^4 \le \Delta h \le \frac{5}{384} \times 0.039 \times L^4 \quad (1)$$

In addition, as shown in FIG. 6B, it is preferable that the height H from the support surface 160a to the top surface 72b of the second wall portion 72 located on the opposite side (Z direction in the diagram) of the support surface 160a is larger by Δh than the height h from the support surface 160a to the top surface 140c of the light receiving portion 140 located on the opposite side (Z direction in the diagram) of the support surface 160a. In other words, it is preferable that the top surface 72b of the second wall portion 72 protrudes from the top surface 140c of the light receiving portion 140 by Δh to the side of the skin 411 as a target. Through such a configuration, the distance (distance between the skin 411 and the top surface 140c of the light receiving portion 140) at which the light receiving portion 140 can accurately receive light having passed through the target (skin 411 of the subject) can be obtained easily and accurately.

Similar to the above, it is more preferable that the difference Δh between the height h from the support surface 160a of the substrate 160 to the top surface 140c of the light receiving portion 140 and the height H from the support surface 160a to the top surface 72b of the second wall portion 72 is set within the range expressed by the following Expression (2). In Expression (2), "0.020" and "0.025" correspond to the coefficient a described above.

$$\frac{5}{384} \times 0.020 \times L^4 \leq \Delta h \leq \frac{5}{384} \times 0.025 \times L^4 \quad (2)$$

Thus, the S/N ratio can be 1 or more by setting the difference Δh between the height h to the top surface 140c of the light receiving portion 140 and the height H to the top surface 72b of the second wall portion 72 within the range expressed by the above Expression (2). In other words, since it is possible to reduce the amount of noise components in the detection signal, it is possible to further acquire the more accurate biological information.

In addition, it has been found that the sensor unit 40 capable of acquiring the accurate biological information can be obtained without having an adverse effect on portability in daily life by setting the width L of the second wall portion 72 in a direction, in which the light receiving portion 140 and the light emitting portion 150 are connected to each other (X-axis direction in the diagram), within the range of 3.0 mm≤L<4.5 mm. Detailed explanation will be given below.

The skin 411 that is a measurement target of the sensor unit 40, for example, a blood vessel as an example of the target to be noted is located about 0.3 mm under the skin. Accordingly, in order that the light receiving portion 140 accurately receives the light reflected from the target, it is advantageous that the width L of the frame is large. However, if the width L of the frame is increased, the area of the biological information measuring module in the planar direction is increased. This has an adverse effect on portability. For example, if the width L of the frame exceeds 4.5 mm, the sensor unit 40 becomes too large. In this case, there is discomfort relevant to wearing. For example, the sensor unit 40 is shifted by shock at the time of exercise. As a result, there is a possibility that portability will become worse. On the other hand, if the width L of the frame is too small, the light receiving area for receiving the light reflected from the skin 411, which is a target, in the light receiving portion 140 is reduced. Accordingly, it is difficult to sufficiently receive the amount of light required for the measurement. Due to such factors, the light receiving portion cannot accurately receive the light reflected from the blood vessel unless the width L of the frame is 0.3 mm or more, for example.

Through the study, the inventors have found the preferable range of the width L of the frame described above, in addition to the difference Δh between the height h of the light receiving portion 140 and the height H of the second wall portion 72 in Expressions (1) and (2) described above. Specifically, it is preferable that the width L of the frame is set within a range of 3.0 mm≤L<4.5 mm. More preferably, the width L of the frame is set within a range of 4.0 mm≤L<4.5.

The verification results of the difference Δh between the height h to the top surface 140c of the light receiving portion 140 and the height H to the top surface 72b of the second wall portion 72 and the width L of the frame are shown in Tables 1 to 6 shown in FIGS. 7 and 8. In Tables 1 to 6, a sensor unit worn on the wrist of the subject was shaken at fixed periods, and the ratio between the pulse signal acquired by the light receiving portion 140 and the power of body motion artifacts was estimated. Hereinafter, the ratio between the pulse signal and the power of body motion artifacts will be described as an "S/N ratio". In Tables 1 to 6, an evaluation result when the S/N ratio is 1 or more is expressed as "preferable (A)", an evaluation result when the S/N ratio is 0.5 to 1 is expressed as "appropriate (B)", an evaluation result when the S/N ratio is 0.5 or less is expressed as "possible (C)" indicating that determination as a pulse signal is possible, and an evaluation result of "non-measurable" showing that determination as a pulse signal is not possible is expressed as "impossible (D)".

As shown in Tables 1 to 6, the evaluation result "preferable (A)" is seen near 7.7 mm, 6.0 mm, 4.0 mm, and 3.0 mm of the width L of the frame. In this case, the value of the coefficient a in Expressions (1) and (2) is 0.020≤a≤0.025. Similarly, the value of the coefficient a when the evaluation result is "appropriate (B)" is 0.016≤a≤0.039. Based on such evaluation results, it is possible to define the preferable and appropriate ranges of the width L of the frame. Although a range of the width L of the frame that is determined to be "preferable (A)" is present near 7.7 mm and 6.0 mm, portability becomes worse as described above if the width L of the frame exceeds 4.5 mm. Accordingly, the width L of the frame that can be appropriately applied is 0.3 mm≤L<4.5 mm. By setting the width L of the frame within the range of 0.3 mm≤L<4.5 mm as described above, it is possible to obtain the sensor unit 40 capable of acquiring the accurate biological information without having an adverse effect on portability in daily life including exercise.

In addition, as shown in Table 4 in FIG. 8, near the width L of the frame of 4.0 mm, it is possible to further widen the range that can be determined to be "preferable (A)". Accordingly, it is possible to perform measurement more appropriately by setting the width L of the frame within the range of 4.0 mm or more. However, since portability become worse if the width L of the frame exceeds 4.5 mm, it can be said that the range of 4.0 mm≤L<4.5 mm is more preferable as described above. By setting the width L of the frame within such a range, it becomes easier to perform accurate measurement of biological information while maintaining portability.

In addition, as described above, it is preferable that the width L of the second wall portion 72 as a frame is the width of the second wall portion 72 in a direction in which the light receiving portion 140 and the light emitting portion 150 are connected to each other (X-axis direction in the diagram). By arranging the light receiving portion 140, the light emitting portion 150, and the second wall portion 72 in this manner, the relationship between the positions of the light receiving portion 140 and the light emitting portion 150 and the width of the second wall portion 72 is defined, and it is possible to acquire more accurate biological information.

Referring to FIGS. 6A and 6B, a resin layer 153 formed of a resin with the translucency such as a transparent resin is provided in a region (hatched in the diagram) between the outer periphery 150b of the light emitting portion 150 and the inner surface 71a of the first wall portion 71, and a resin layer 149 formed of a transparent resin is provided in a region (hatched in the diagram) between the outer periphery 140b of the light receiving portion 140 and the inner surface 72a of the second wall portion 72. Since the frame-shaped first and second wall portions 71 and 72 as in the present configuration are provided, resin is dammed by the first and second wall portions 71 and 72. Therefore, since the flow of resin to the outside can be prevented, resin filling can be easily realized. Since the strength of the first and second wall portions 71 and 72 can be increased by the resin layers 153 and 149 provided in this manner, the strength of the sensor unit 40 can also be increased. In addition, the resin layers 153 and 149 may be provided in at least one of the region between the outer periphery 150b of the light emitting portion 150 and the inner surface 71a of the first wall portion 71 and the region between the outer periphery 140b of the light receiving portion 140 and the inner surface 72a of the second wall portion 72. Also in this case, the same effect is obtained.

In addition, it is preferable that the sectional shapes of the top surfaces 71b and 72b, which are upper open end surfaces of the first and second wall portions 71 and 72, are smooth shapes without a corner, for example, curved shapes such as circular arc shapes. By forming the sectional shapes of the top surfaces 71b and 72b as curved shapes, when the first and second wall portions 71 and 72 are in contact with a user (body) who is a measurement target, curved portions (rounded surfaces) of the first and second wall portions 71 and 72 are in contact with the user (body). Accordingly, for example, embedding in the skin of the user is less likely to occur. Therefore, it is possible to reduce discomfort. As a result, it is possible to improve the fit of the user when the user wears the sensor unit 40 as a sensor module or a biological information measuring device in which the sensor unit 40 is mounted.

A connection terminal 274 that is electrically connected to a control unit (not shown) is provided on the support surface 160a of the substrate 160 (sensor substrate) as a support portion. The connection terminal 274 is a terminal for making an electrical connection, and can be formed by performing gold (Au) plating on a metal layer, for example, a copper (Cu) layer. By providing such a connection terminal 274 on the substrate 160, it is possible to connect a support portion to, for example, a control unit in a compact manner.

Anti-reflection processing may be performed on at least the surface of the wall portion 70 or the second wall portion 72 on the light receiving portion 140 side. For example, the color of the surface (internal surface or the like) of the wall portion 70 may be a predetermined color, such as black, so that the diffused reflection of light is prevented. Alternatively, the surface of the wall portion 70 may be made to have a moth-eye structure. For example, an anti-reflection structure is formed by forming a structure of irregularities having a gap of tens to hundreds of nanometer (nm) therebetween on the surface. Through such anti-reflection processing, for example, it is possible to effectively suppress a situation in which light reflected by the surface of the wall portion 70 becomes stray light and becomes a noise component of the detection signal.

As described above, the light receiving portion 140, the light emitting portion 150, and the wall portion 70 are mounted on the substrate 160. The substrate 160 is a rigid substrate, for example. Terminals (not shown) for connection with signal and power terminals (not shown) of the light receiving portion 140 or terminals (not shown) for signal and power connection with an external main substrate are provided on the substrate 160. For example, the terminal of the light receiving portion 140 and the terminal of the substrate 160 are connected by wire bonding or the like. Thus, since the light receiving portion 140, the light emitting portion 150, the wall portion 70, and the like are mounted (supported) on the substrate 160, the distance between each of the light emitting portion 150 and the light receiving portion 140 and the measurement target is reduced. Accordingly, since it is possible to reduce the amount of noise mixed in the light, it is possible to improve the measurement accuracy.

Figure 5A:
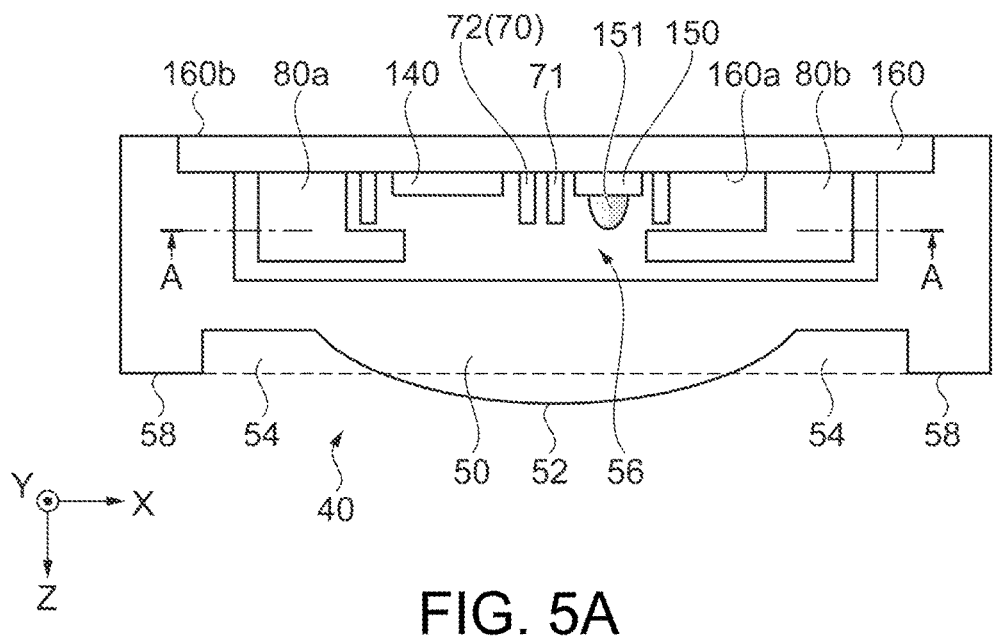
FIGS. 5A and 5B show Configuration Example 1 of a sensor unit as a biological information measuring module, where
Figure 5B:
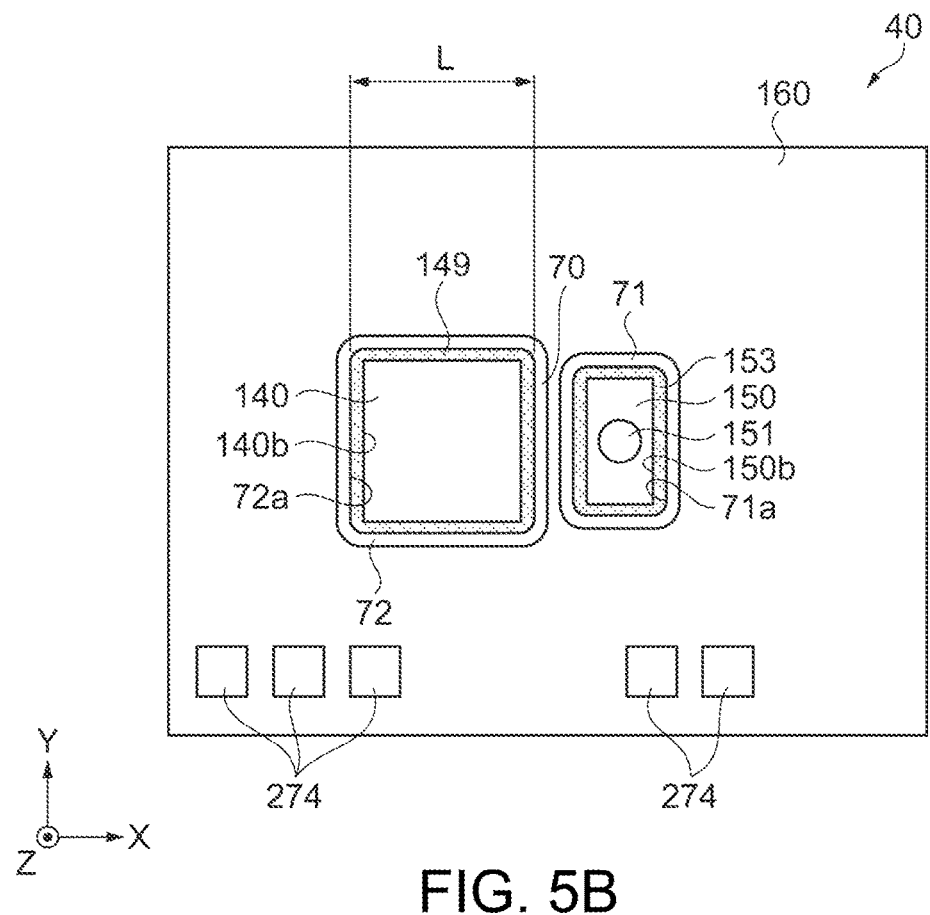
Figure 6A:
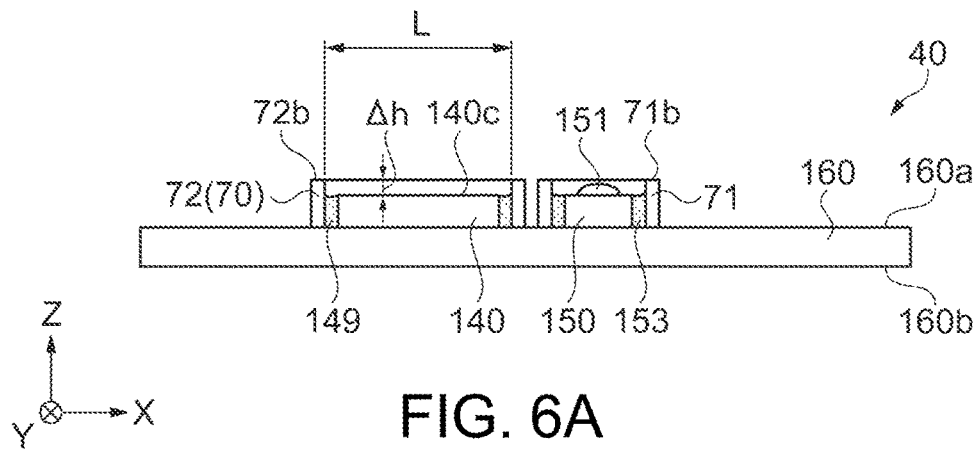
FIGS. 6A and 6B show Configuration Example 1 of the sensor unit, where
Figure 6B:
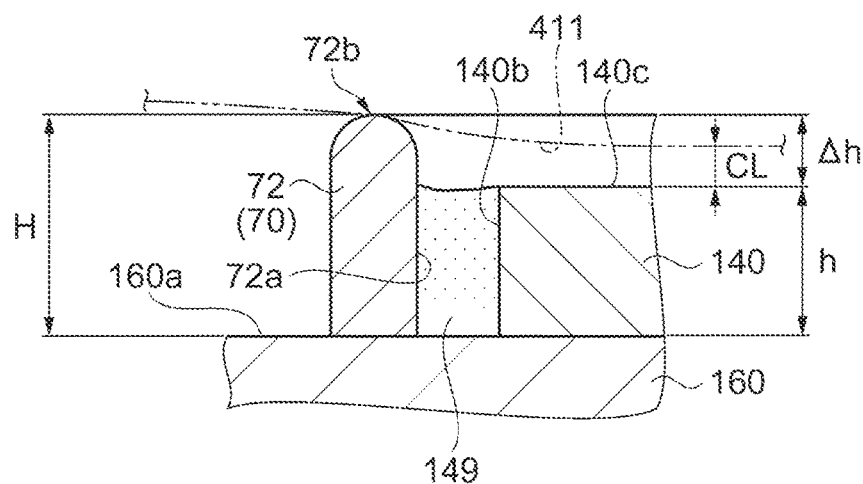

In addition, as shown in FIG. 5A, the diaphragm portions 80a and 80b may be provided in the sensor unit 40. The diaphragm portion 80 focuses the light from the subject or the light from the light emitting portion 150 on the optical path between the subject and the sensor unit 40. In FIG. 5A, the diaphragm portions 80a and 80b are provided between the light-transmissive member 50 and the light emitting portion 150. However, the diaphragm portions 80a and 80b may be provided between the light-transmissive member 50 and the subject, or may be provided in the light-transmissive member 50.

The light-transmissive member 50 shown in FIG. 5A is provided on the surface of the biological information measuring device on a side in contact with the subject, and light from the subject is transmitted through the light-transmissive member 50. The light-transmissive member 50 is in contact with the subject additionally when measuring the biological information of the subject. For example, the protruding portion 52 (detection window) of the light-transmissive member 50 is in contact with the subject. The surface shape of the protruding portion 52 is preferably a curved shape (spherical shape), but various shapes can be adopted without being limited thereto. Any light-transmissive member 50 through which the light from the subject is transmitted can be used. In addition, a transparent material may be used, or a colored material may be used.

The groove 54 for suppressing a pressure fluctuation or the like is provided around the periphery of the protruding portion 52 of the light-transmissive member 50. Assuming that the surface of the light-transmissive member 50 on a side where the protruding portion 52 is provided is a first surface, the light-transmissive member 50 has the recess 56 at a position corresponding to the protruding portion 52 on a second surface of the back side of the first surface. The light receiving portion 140, the light emitting portion 150, the wall portion 70, and the diaphragm portions 80a and 80b are provided in the space of the recess 56.

On the surface of the biological information measuring device on the subject side, the pressure suppressing portion 58 for suppressing the pressure given to the subject (skin of the wrist) by the protruding portion 52 is provided. In FIGS. 5A and 5B, the pressure suppressing portion 58 is provided so as to surround the protruding portion 52 of the light-transmissive member 50. In addition, the protruding portion 52 protrudes to the subject side from the pressure suppressing portion (pressure suppressing surface) 58.

By providing such a protruding portion 52, for example, it is possible to apply the initial pressure to exceed a vein vanishing point to the subject. In addition, by providing the pressure suppressing portion 58 for suppressing the pressure given to the subject by the protruding portion 52, it is possible to suppress the pressure fluctuation to the minimum in the use range where the biological information measuring device measures the biological information. Therefore, it is possible to reduce the amount of noise components or the like. In addition, if the protruding portion 52 protrudes from the pressure suppressing portion 58, the protruding portion 52 is in contact with the subject to give initial pressure, and then the pressure suppressing portion 58 is in contact with the subject. Accordingly, it is possible to suppress the pressure given to the subject by the protruding portion 52. Here, the vein vanishing point is a point where a signal caused by the vein, which is superimposed on the pulse wave signal, is lost or becomes weak enough not to affect pulse wave measurement when the protruding portion 52 is in contact with the subject and the pressure is gradually increased.

According to the configuration of the first embodiment described above, by defining the relationship between the light receiving portion 140 and the second wall portion 72 as a frame, it is possible to obtain the distance between the target and the light receiving portion 140 at which the light receiving portion 140 can accurately receive the light having passed through the measurement target (for example, the skin 411 or a blood vessel (not shown)). Therefore, it is possible to accurately acquire biological information, such as a pulse wave. In addition, it is possible to obtain the sensor unit 40 as a biological information measuring module capable of acquiring the accurate biological information without having an adverse effect on portability in daily life, when performing hard exercise, and the like.

Modification Example of the Sensor Unit

Figure 9:
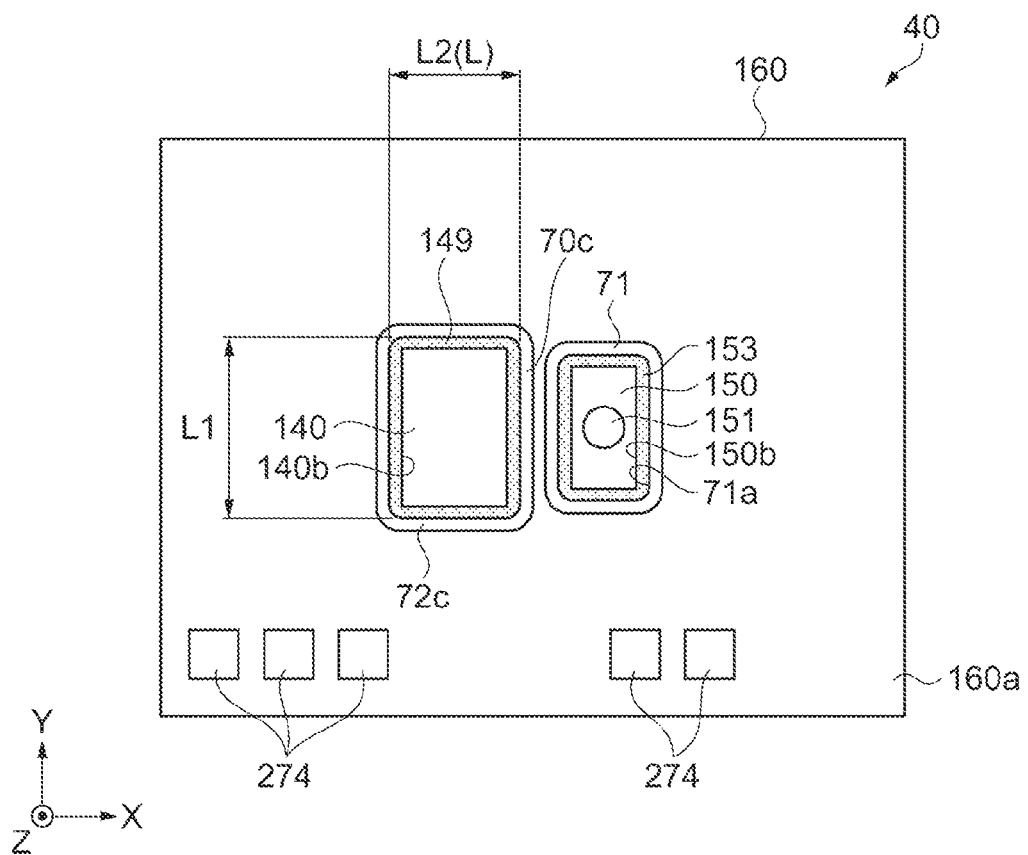
FIG. 9 is a plan view showing Modification Example 1 of the sensor unit.
Figure 10:
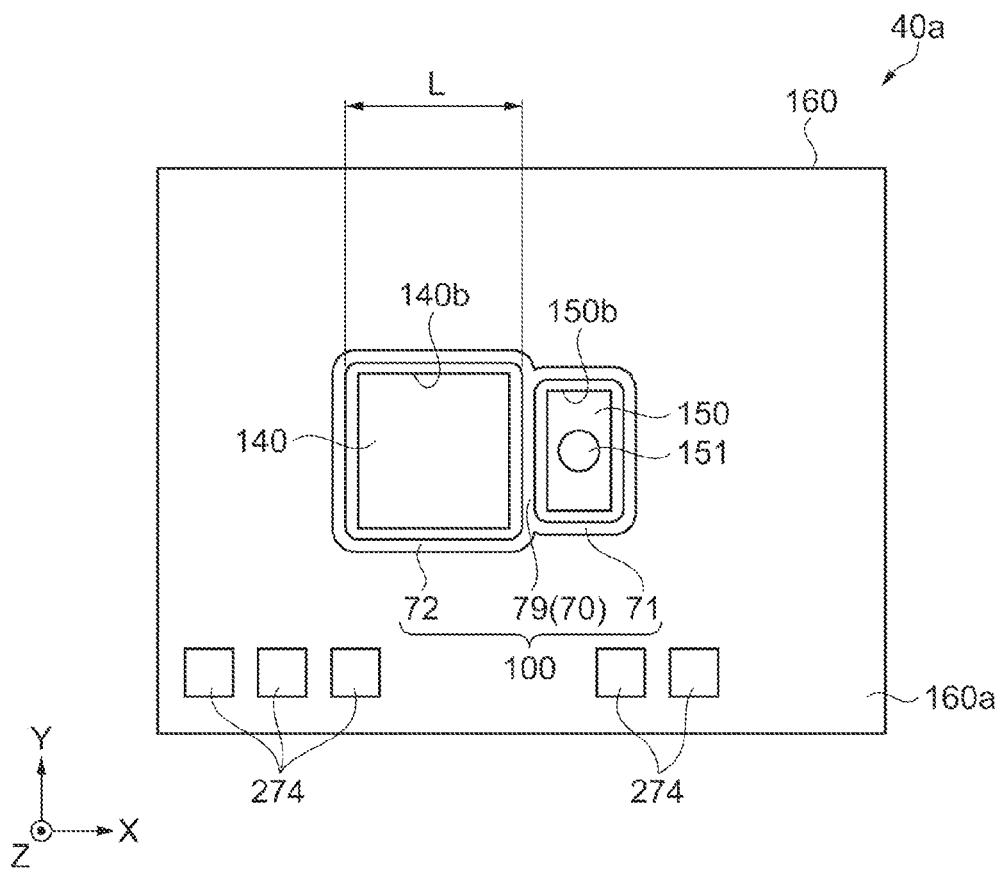
FIG. 10 is a plan view showing Modification Example 2 of the sensor unit.

Next, a modification example of the sensor unit 40 will be described with reference to FIGS. 9 and 10. FIG. 9 is a plan view showing Modification Example 1 of the sensor unit, and FIG. 10 is a plan view showing Modification Example 2 of the sensor unit. In FIGS. 9 and 10, the arrangement of the light receiving portion 140, the light emitting portion 150, and the first and second wall portions 71 and 72 as frames are shown in the center, and other components are not shown. The same components as in the first embodiment described above are denoted by the same reference numerals, and the explanation thereof will be omitted. Also in the following modification examples, the width L of the second wall portion 72 and the difference Δh between the height h of the light receiving portion 140 and the height H of the second wall portion 72 can be similarly applied.

Modification Example 1

First, Modification Example 1 of the sensor unit 40 will be described with reference to FIG. 9. In the configuration of the Modification Example 1, the configuration of the second wall portion is different from that in the configuration of the first embodiment described above. The second wall portion 72 of the first embodiment described above has an outer shape in plan view as an approximately square shape. In contrast, a second wall portion 72c in the Modification Example 1 has a so-called rectangular shape in which the width L2 (L) in a direction in which the light receiving portion 140 and the light emitting portion 150 are connected to each other (X-axis direction in the diagram) is different from the width L1 in a direction (Y-axis direction in the diagram) perpendicular to the direction. Specifically, the second wall portion 72c is configured such that the width L2 in the X-axis direction is smaller than the width L1 in the Y-axis direction. In addition, the width L2 (L) of the second wall portion 72c in the short side direction is a width in a direction in which the light receiving portion 140 and the light emitting portion 150 are connected to each other.

Thus, by setting the width L2 (L) of the second wall portion 72c in the short side direction as a width in a direction in which the light receiving portion 140 and the light emitting portion 150 are connected to each other, it is possible to define the width (width L2 (L)) of the frame in the short side direction of the rectangular shape, which is dominant with respect to the deformation of the target. Therefore, it is possible to provide the sensor unit 40 that can acquire the accurate biological information without having an adverse effect on portability.

Modification Example 2

Next, Modification Example 2 of the sensor unit 40 will be described with reference to FIG. 10.

In the sensor unit 40 of the first embodiment described above, the first and second wall portions 71 and 72 are separately provided. In contrast, in a wall portion 100 as a frame in a sensor unit 40a of the Modification Example 2, a first wall portion 71 surrounding the outer periphery 150b of the light emitting portion 150 and a second wall portion 72 surrounding the outer periphery 140b of the light receiving portion 140 are connected to a center wall 79 (70) provided between the light emitting portion 150 and the light receiving portion 140. In other words, a structure in which a wall of the first wall portion 71 on the light emitting portion 150 side and a wall of the second wall portion 72 on the light receiving portion 140 side in Configuration Example 2 of the first embodiment described above are integrally formed through the center wall 79 is the wall portion 100 in this modification example.

In such a wall portion 100 as a frame, since the first and second wall portions 71 and 72 are connected to each other through the center wall 79, it is possible to achieve space saving and to improve assembling efficiency. Therefore, since it is possible to reduce the area occupied by the wall portion 100, it is possible to form the sensor unit 40a that is more compact and is excellent in portability.

Configuration Example 2 of the Sensor Unit

Figure 11A:
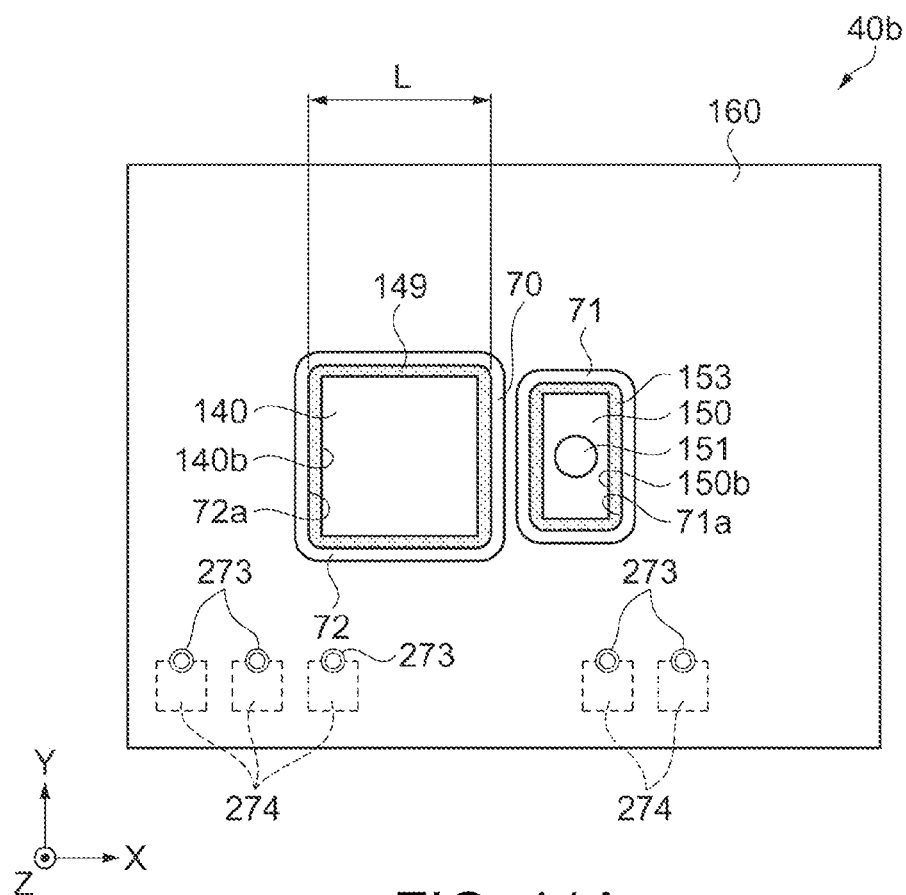
FIGS. 11A and 11B show Configuration Example 2 of the sensor unit as a biological information measuring module, where
Figure 11B:
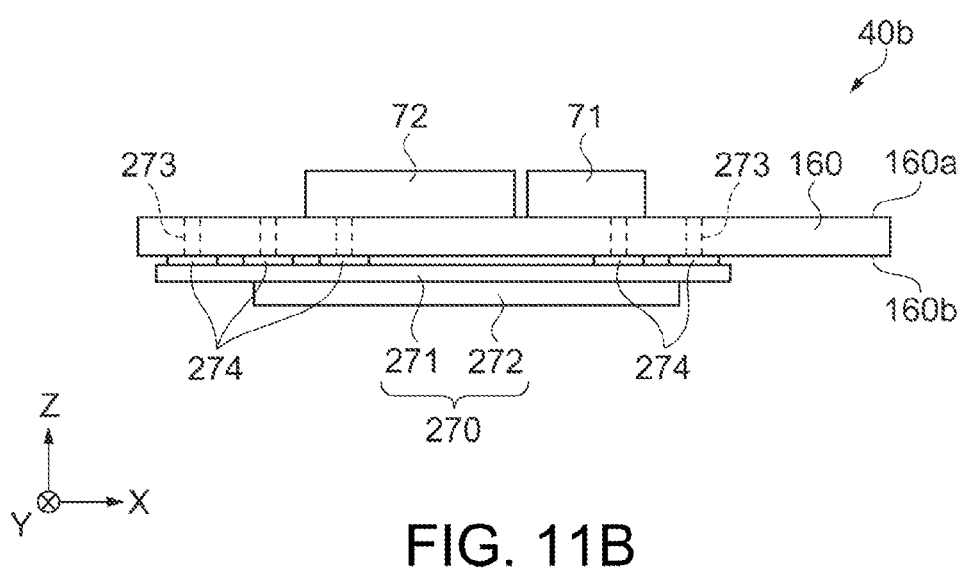

Next, Configuration Example 2 of the sensor unit 40 will be described with reference to FIG. 11. FIGS. 11A and 11B show Configuration Example 2 of the sensor unit as a biological information measuring module. FIG. 11A is a plan view seen from the same direction as the line A-A in FIG. 5A, and FIG. 11B is a front sectional view of FIG. 11A. In addition, the same components as in the first embodiment described above are denoted by the same reference numerals, and the explanation thereof will be omitted. Also in the following Configuration Example 2, the width L of the second wall portion 72 and the difference Δh between the height h of the light receiving portion 140 and the height H of the second wall portion 72 can be similarly applied.

A sensor unit 40b in Configuration Example 2 includes the light receiving portion 140 and the light emitting portion 150 as in the first embodiment, and includes a control unit 270. The light receiving portion 140 and the light emitting portion 150 are aligned with a predetermined gap interposed therebetween, and are mounted on the support surface 160a (mounting surface) of the substrate 160 (sensor substrate) as a support portion. In addition, the first and second wall portions 71 and 72 as frames surrounding the outer periphery 140b of the light receiving portion 140 and the outer periphery 150b of the light emitting portion 150 are provided. Since these components are the same as those in the first embodiment, the detailed explanation thereof will be omitted.

In the substrate 160, a through hole 273 connecting the support surface 160a and a back surface 160b, which are front and back surfaces of the substrate 160, to each other is provided. The through hole 273 and the light receiving portion 140 and the light emitting portion 150 are connected to each other by electrical wiring (not shown). The connection terminal 274 connected to the through hole 273 is provided on the back surface 160b. The connection terminal 274 is a terminal for making an electrical connection, and can be formed by performing gold (Au) plating on a metal layer, for example, a copper (Cu) layer.

The control unit 270 includes a circuit board 271 as a base portion and a circuit element 272 mounted on the circuit board 271. The control unit 270 can include, for example, the processing unit 200, the storage unit 240, the communication unit 250, and the like described in the first embodiment. Accordingly, the control unit 270 can have at least a function of controlling the transmission and reception of light for detecting biological information, such as a pulse wave, or a function of performing signal processing. The control unit 270 is connected to the back surface 160*b* side of the substrate 160 by connection based on electrical conduction between a terminal (not shown) of the circuit board 271 and the connection terminal 274 of the substrate 160.

According to the sensor unit 40*b* having such a configuration, the substrate 160 and the control unit 270 can be connected to each other by the connection terminal 274 that is provided on the back surface 160*b* of the substrate 160 as a support portion through the through hole 273. Thus, for example, the light receiving portion 140, the light emitting portion 150, the first wall portion 71, and the second wall portion 72 can be disposed on the support surface 160*a* side of the substrate 160, and the control unit 270 can be disposed on the back surface 160*b* side. Through such arrangement, it is possible to realize the sensor unit 40*b* as a biological information measuring module that can realize space saving and miniaturization.

In addition, it is preferable that the thickness of the substrate 160 as a support portion is larger than the thickness of the circuit board 271 as a base portion of the control unit 270. Thus, since the thickness of the substrate 160 is made to be large, the base portion (circuit board 271) of the control unit 270 is supported by the support portion (substrate 160) having high strength. Therefore, it is possible to increase the strength of the sensor unit 40*b* (biological information measuring module).

The biological information measuring device according to the present embodiment configured as described above includes the sensor units 40, 40*a*, and 40*b* as biological information measuring modules that can perform detection (measurement) more accurately and that are small and are excellent in portability. Therefore, it is possible to realize the biological information measuring device that can stably detect biological information and that is small and is excellent in portability.

Second Embodiment

Next, a second embodiment of the invention will be described with reference to the accompanying diagrams.

A biological information measuring device according to the second embodiment is a heart rate monitoring device that is mounted on the body (for example, human body), of which biological information is to be measured, to measure the biological information, such as a pulse (heart rate), as in the first embodiment described above. In each diagram shown below, in order to make each component recognizable in the diagram, the size or proportion of each component may be appropriately described so as to be different from the actual size or proportion of the component. Also in the following second to fifth embodiments, the width L of the second wall portion 72 as a frame described in the first embodiment and the difference Δh between the height h of the light receiving portion 140 and the height H of the second wall portion 72 can be similarly applied.

First, before describing a heart rate monitoring device 1010 as the biological information measuring device according to the second embodiment, a known example of the heart rate monitoring device as the biological information measuring device according to the second embodiment will be described with reference to FIG. 12.

Figure 12:
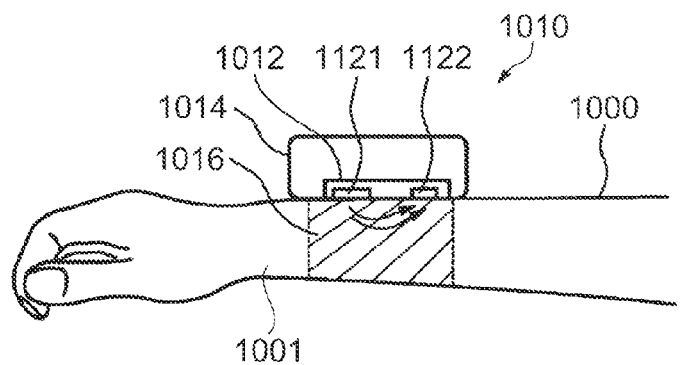
FIG. 12 is a sectional view showing a known example of a biological information measuring device according to a second embodiment.

FIG. 12 is a sectional view showing the heart rate monitoring device 1010 as a biological information measuring device in the related art that measures physiological parameters (biological information) of a user (subject) 1000 (in this diagram, the arm of the user) wearing the heart rate monitoring device. The heart rate monitoring device 1010 includes a sensor 1012, which measures the heart rate as at least one physiological parameter of the user 1000, and a case 1014 in which the sensor 1012 is housed. The heart rate monitoring device 1010 is worn on the arm 1001 of the user 1000 using a fixing unit 1016 (for example, a band).

The sensor 1012 includes a light emitting element 1121 as a light emitting portion and a light receiving element 1122 as a light receiving portion, which are two sensor elements, and is a heart rate monitoring sensor for measuring or monitoring the heart rate. However, the sensor 1012 may be a sensor that measures one or more physiological parameters (for example, a heart rate, blood pressure, expiratory volume, skin conductance, and skin humidity). When the case 1014 includes a band type housing, the heart rate monitoring device 1010 can be used as a wrist watch type monitoring device used in sports, for example. In addition, the case 1014 can be formed in any form that mainly allows the sensor 1012 to be held in a desired position of the user 1000, and additional elements, such as a battery, a processing unit, a display, and a user interface, may be optionally housed.

The biological information measuring device in the related art is the heart rate monitoring device 1010 for monitoring the heart rate of the user. In addition, the sensor 1012 is an optical sensor configured to include the light emitting element 1121 and the light receiving element 1122. The optical heart rate monitor using an optical sensor depends on the light emitting element 1121 (typically, an LED is used) as a light source that emits light to the skin. Some of light beams emitted from the light emitting element 1121 to the skin are absorbed by the blood flowing through the blood vessel under the skin, but the remaining light beams are reflected to exit the skin. Then, the reflected light is captured by the light receiving element 1122 (typically, a photodiode is used). The light receiving signal from the light receiving element 1122 is a signal including information corresponding to the amount of blood flowing through blood vessels. The amount of blood flowing through blood vessels changes with the pulsation of the heart. Thus, the signal on the light receiving element 1122 changes corresponding to the pulsation of the heart. That is, the change in the signal of the light receiving element 1122 is equivalent to the heart rate pulse. By counting the number of pulses per unit time (for example, per 10 seconds), it is possible to obtain the number of heart beats in one minute (that is, a heart rate).

Figure 13:
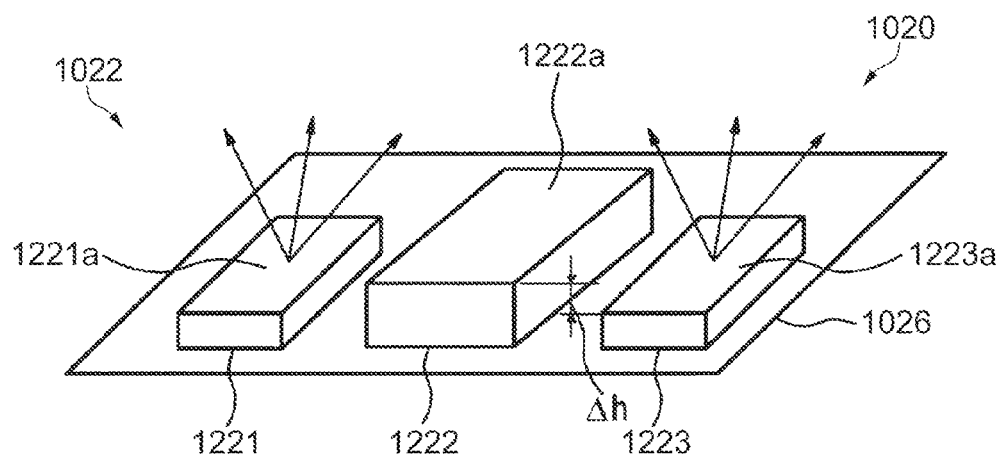
FIG. 13 is a perspective view showing the biological information measuring device according to the second embodiment.

Hereinafter, a heart rate monitoring device 1020 as the biological information measuring device according to the second embodiment will be described with reference to FIG. 13. FIG. 13 is a perspective view showing a heart rate monitoring device as the biological information measuring device according to the second embodiment. Although not shown in FIG. 13, the heart rate monitoring device 1020 as the biological information measuring device according to the second embodiment is worn on the arm of the user using a fixing unit, such as a band, as in the first embodiment described above.

In the heart rate monitoring device 1020 as the biological information measuring device according to the second embodiment, light emitting elements 1221 and 1223 as a plurality of light emitting portions (in this example, two light emitting portions) and a light receiving element 1222 as one light receiving portion are aligned in a row. Specifically, the heart rate monitoring device 1020 includes a sensor 1022 including at least two sensor elements (in this example, two light emitting elements 1221 and 1223 as first and second light emitting portions and the light receiving element 1222 as a light receiving portion are used as three sensor elements). Although not shown, it is desirable that the first and second wall portions 71 and 72 (refer to FIGS. 5A to 6B) having the same configuration as in the first embodiment described above are provided between the light receiving element 1222 and the light emitting element 1221 and between the light receiving element 1222 and the light emitting element 1223.

The light receiving element 1222 as a light receiving portion is disposed between the two light emitting elements 1221 and 1223 as first and second light emitting portions. The two light emitting elements 1221 and 1223 as first and second light emitting portions are disposed at axisymmetrical positions with respect to the virtual line passing through the center of the light receiving element 1222 as a light receiving portion. By arranging the light emitting elements 1221 and 1223 and the light receiving element 1222 as described above, dead space is reduced. Accordingly, it is possible to achieve space saving. In addition, since light beams from the first and second light emitting portions located at axisymmetrical positions are collected by the light receiving portion, it is possible to perform more exact detection.

The sensor element detects a sensor signal. The sensor 1022 includes an optical sensor, which is formed by the light emitting elements 1221 and 1223 using two LEDs for emitting light to the skin of the user, and at least one light receiving element 1222 (photodiode) for receiving the light reflected from the skin. The heart rate monitoring device 1020 includes a case or a housing (not shown). The case or the housing may be similar to or the same as the case 1014 shown in FIG. 12, or may be similar to or the same as the case unit 30 in the first embodiment described above.

In addition, the sensor 1022 is supported on one surface of a carrier (substrate) 1026. Here, a configuration including the carrier (substrate) 1026 and the sensor 1022 supported on the carrier (substrate) 1026 corresponds to the biological information measuring module. This is the same as in the following third to fifth embodiments. Light emitted from the light emitting elements 1221 and 1223 is reflected without being absorbed by the skin or the like, and can reach the light receiving element 1222 directly. In the heart rate monitoring device 1020, the distance between the carrier 1026 and the upper surfaces 1221a and 1223a of the light emitting elements 1221 and 1223 is smaller than the distance between the carrier 1026 and the upper surface 1222a of the light receiving element 1222. That is, the difference between the distance between the carrier 1026 and the upper surfaces 1221a and 1223a of the light emitting elements 1221 and 1223 and the distance between the carrier 1026 and the upper surface 1222a of the light receiving element 1222 is Δh. The light receiving element 1222 receives light from the upper surface 1222a that is a top surface. According to these configurations, most of the light emitted from the light emitting elements 1221 and 1223 travels toward the skin. Therefore, there is an effect that the reflected light is directly incident on the light receiving element 1222 without an air layer or the like. In other words, since the light receiving element 1222 is in close contact with the skin, it is possible to realize a structure in which a gap between the upper surface (light receiving surface) 1222a of the light receiving element 1222 and the skin is less likely to be generated. Therefore, it is possible to suppress light serving as a noise source, such as ambient light, from being incident on the upper surface 1222a. In addition, light from the light emitting elements 1221 and 1223 that does not pass through the skin, for example, light that is directly incident on the light receiving element 1222 from the light emitting elements 1221 and 1223, cannot reach the upper surface 1222a of the light receiving element 1222.

Third Embodiment

Figure 14:
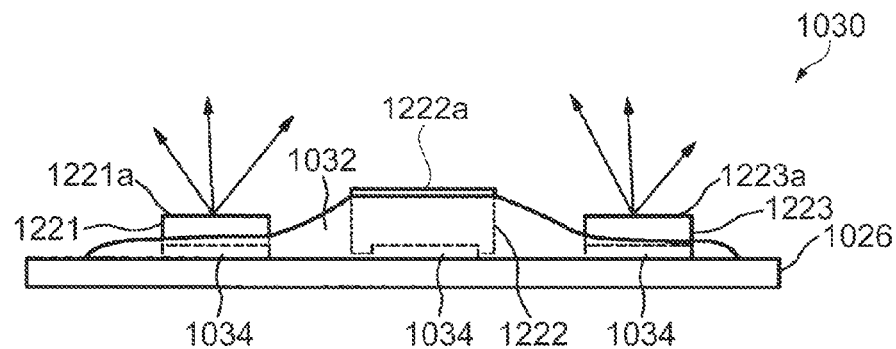
FIG. 14 is a front view showing a biological information measuring device according to a third embodiment.

Next, a heart rate monitoring device 1030 as a biological information measuring device according to a third embodiment will be described with reference to FIG. 14. FIG. 14 is a front view showing a heart rate monitoring device as the biological information measuring device according to the third embodiment. Although not shown in FIG. 14, the heart rate monitoring device 1030 as the biological information measuring device according to the third embodiment is worn on the arm of the user using a fixing unit, such as a band, as in the first embodiment described above.

As shown in FIG. 14, electrical connection terminals 1034 of the light emitting elements 1221 and 1223 as light emitting portions and the light receiving element 1222 as a light receiving portion should be preferably covered with an insulating material (for example, epoxy resin) 1032 for the protection of electrical components. In addition, the light emitting elements 1221 and 1223 or the light receiving element 1222 may not be covered with the insulating material 1032. Specifically, a region between the light emitting element 1221 and the light receiving element 1222 and a region between the light emitting element 1223 and the light receiving element 1222 can be filled with the insulating material 1032. In other words, at least the upper surface 1222a of the light receiving element 1222 and the upper surfaces 1221a and 1223a of the light emitting elements 1221 and 1223 cannot be covered with the insulating material 1032. Through such a configuration, it is possible to suppress interference by an air gap between the skin and the light emitting elements 1221 and 1223. In addition, the insulating material 1032 may cover the upper surfaces 1221a and 1223a of the light emitting elements 1221 and 1223 and the upper surface 1222a of the light receiving element 1222. By adopting the configuration described above, it is possible to protect the upper surface 1222a of the light receiving element 1222 in contact with the skin or the upper surfaces 1221a and 1223a of the light emitting elements 1221 and 1223. Therefore, it is possible to prevent damage to the upper surface 1222a of the light receiving element 1222 or the upper surfaces 1221a and 1223a of the light emitting elements 1221 and 1223. In this case, the insulating material 1032 can also be regarded as a protective film.

In the heart rate monitoring device 1030 as the biological information measuring device according to the third embodiment, the insulating material 1032 using an epoxy resin is provided as a generally possible example. In FIG. 14, the insulating material 1032 is disposed without covering the upper surfaces 1221a and 1223a of the light emitting elements 1221 and 1223, and protects the electrical connection terminal 1034. Light emitted from the light emitting elements 1221 and 1223 is expressed by an arrow.

Thus, by arranging the insulating material 1032 to the minimum extent that does not interfere with the correct functioning of the heart rate monitoring device 1030 so that the electrical connection terminals 1034 of the light emitting elements 1221 and 1223 and the light receiving element 1222 are protected, it is possible to further improve the heart rate monitoring device 1030. Although not shown, it is more preferable that the first and second wall portions 71 and 72 (refer to FIGS. 5A to 6B) having the same configuration as in the first embodiment described above are provided between the light receiving element 1222 and the light emitting element 1221 and between the light receiving element 1222 and the light emitting element 1223.

Figure 15:
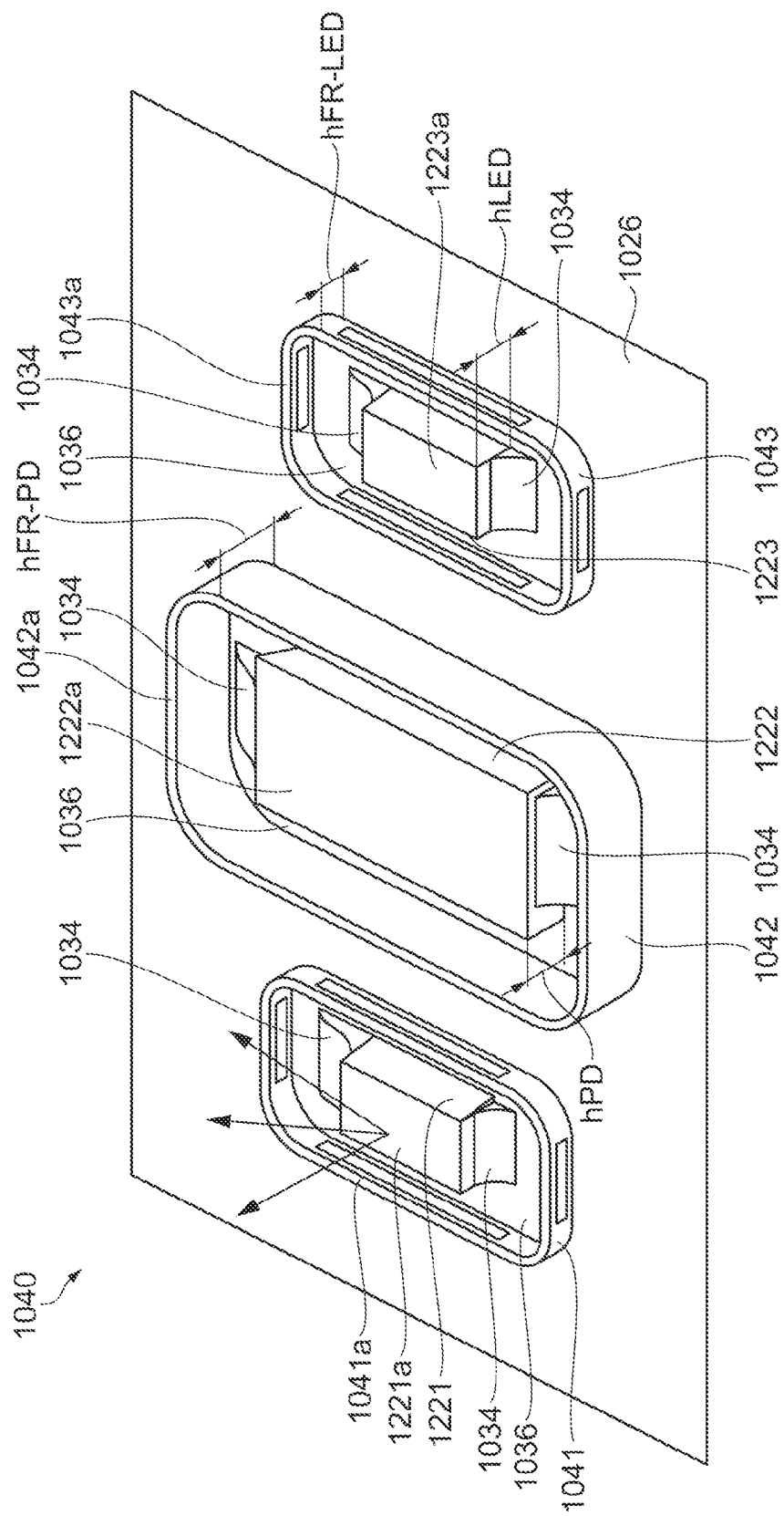
FIG. 15 is a perspective view showing a biological information measuring device according to a fourth embodiment.

In addition, it is more preferable to form a heart rate monitoring device 1040 as a biological information measuring device according to a fourth embodiment as shown in FIG. 15 by adopting the injection of the epoxy resin in the third embodiment.

Fourth Embodiment

Next, the heart rate monitoring device 1040 as the biological information measuring device according to the fourth embodiment will be described with reference to FIG. 15. FIG. 15 is a perspective view showing a heart rate monitoring device as the biological information measuring device according to the fourth embodiment. Although not shown in FIG. 15, the heart rate monitoring device 1040 as the biological information measuring device according to the fourth embodiment is worn on the arm of the user using a fixing unit, such as a band, as in the first embodiment described above.

In the heart rate monitoring device 1040 as the biological information measuring device according to the fourth embodiment, frames 1041, 1042, and 1043 are disposed. The frames 1041, 1042, and 1043 are disposed around the light emitting elements 1221 and 1223 as light emitting portions and the light receiving element 1222 as a light receiving portion, and gaps 1036 between the frames 1041, 1042, and 1043 and the light emitting elements 1221 and 1223 and the light receiving element 1222 are formed. An insulating material (not shown in FIG. 15) is injected by using the frames 1041, 1042, and 1043 as guides, and the electrical connection terminals 1034 of the light emitting elements 1221 and 1223 and the light receiving element 1222 are covered.

In the example shown in the fourth embodiment, the light emitting elements 1221 and 1223 and the light receiving element 1222 are surrounded by the separate frames 1041, 1042, and 1043. As another example, all of the frames 1041, 1042, and 1043 may be connected to each other, or all sensor elements may be surrounded by a unitary frame. Each of the frames 1041, 1042, and 1043 can be used as a light blocking wall as an example of the light blocking portion. By using the frames 1041, 1042, and 1043 as light blocking walls, it is possible to prevent light emitted from the light emitting elements 1221 and 1223 from being directly incident on the light receiving element 1222.

As improvements not affecting the function of the heart rate monitoring device 1040, it is preferable that upper edges 1041a and 1043a of the frames 1041 and 1043 around the light emitting elements 1221 and 1223 are lower than the upper surfaces 1221a and 1223a of the light emitting elements 1221 and 1223. In other words, a distance hFR-LED between the carrier 1026 and the upper edges 1041a and 1043a of the separate frames 1041 and 1043 is equal to or less than a distance hLED between the carrier 1026 and the upper surfaces 1221a and 1223a of the light emitting elements 1221 and 1223 surrounded by the separate frames 1041 and 1043 (hFR-LED≤hLED).

Preferably, a difference between the distance hLED between the carrier 1026 and the upper surfaces 1221a and 1223a of the light emitting elements 1221 and 1223 and the distance hFR-LED between the carrier 1026 and the upper edges 1041a and 1043a of the separate frames 1041 and 1043 is set in the range of 0.1 mm to 0.8 mm. More preferably, the difference between the distance hLED between the carrier 1026 and the upper surfaces 1221a and 1223a of the light emitting elements 1221 and 1223 and the distance hFR-LED between the carrier 1026 and the upper edges 1041a and 1043a of the separate frames 1041 and 1043 is set in the range of 0.2 mm to 0.5 mm.

In addition, it is preferable that an upper edge 1042a of a frame (receiver frame) 1042 around the light receiving element 1222 is higher than the upper surface 1222a of the light receiving element 1222. In other words, a distance hFR-PD between the carrier 1026 and the upper edge 1042a of the frame 1042 is larger than a distance hPD between the carrier 1026 and the upper surface 1222a of the light receiving element 1222 surrounded by the frame 1042 (hFR-PD>hPD).

Preferably, a difference between the distance hPD between the carrier 1026 and the upper surface 1222a of the light receiving element 1222 and the distance hFR-PD between the carrier 1026 and the upper edge 1042a of the frame 1042 is set in the range of 0 mm to 0.5 mm. More preferably, a difference between the distance hPD between the carrier 1026 and the upper surface 1222a of the light receiving element 1222 and the distance hFR-PD between the carrier 1026 and the upper edge 1042a of the frame 1042 is set in the range of 0.1 mm to 0.2 mm.

In addition, the distance hFR-PD between the carrier 1026 and the upper edge 1042a of the frame 1042 is larger than the distance hLED between the carrier 1026 and the upper surfaces 1221a and 1223a of the light emitting elements 1221 and 1223 (hFR-PD>hLED).

For example, when the light receiving element 1222 and the light emitting elements 1221 and 1223 are close to each other, it is possible to adopt a configuration in which only one frame wall is present between the light receiving element 1222 and the light emitting elements 1221 and 1223. This may happen for the reasons of ease of manufacture. When the one frame wall is a case, frame walls of both frames in the light receiving element 1222 and the light emitting elements 1221 and 1223 match each other. This means that the frame walls of the light emitting elements 1221 and 1223 are higher. Specifically, of the frames 1041 and 1043 surrounding the light emitting elements 1221 and 1223, a frame wall on a side where there is the light receiving element 1222 becomes high, and the other frame wall become lower than the upper surfaces 1221a and 1223a of the light emitting elements 1221 and 1223.

Instead of the frames 1041, 1042, and 1043, a first wall portion may be provided between the light receiving element 1222 and the light emitting element 1221 or the light emitting element 1223, and a second wall portion may be provided outside the light emitting elements 1221 and 1223, that is, on a side of the light receiving element 1222 opposite the first wall portion.

Figure 16:
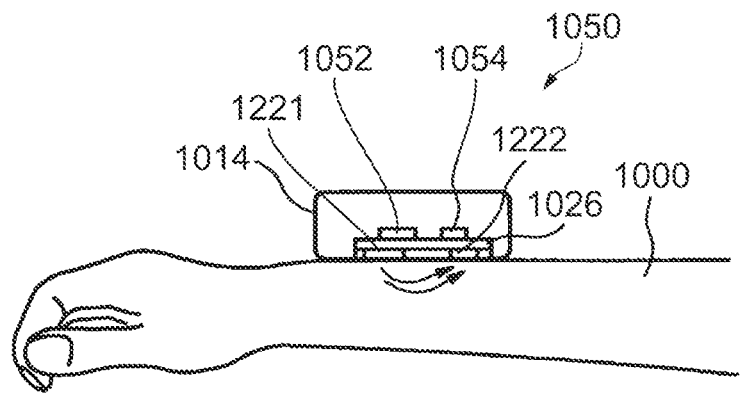
FIG. 16 is a sectional view showing a biological information measuring device according to a fifth embodiment.

In this case, the distance between the carrier 1026 and the upper surface of the first wall portion may be larger than the distance between the carrier 1026 and the upper surface of the second wall portion. By adopting such a configuration, it is possible to realize the function of the frame with a smaller number of members, compared with a case in which the light emitting element or the light receiving portion is configured to be surrounded as shown in FIG. 16.

In addition, by using the frames 1041 and 1043 or the frame 1042 as in the fourth embodiment, it is possible to prevent an insulating material, such as injected epoxy resin, from flowing to the outside. Preventing the outflow of insulating material such as epoxy resin or the like by generating the additional structure as described above is an option that enables high productivity. In addition, the frames 1041 and 1043 or the frame 1042 may be formed of the same material as the carrier 1026. For example, a frame may be formed by injection molding using an epoxy-based resin or a polycarbonate-based resin.

As described above, the insulating material 1032 (refer to FIG. 14) serves to protect the electrical connection terminals 1034 of sensor elements (the light emitting elements 1221 and 1223 and the light receiving element 1222). However, the electrical connection terminals 1034 have to be further in contact with additional electronic devices (for example, a driver, detection electronics, a processor, or a power supply) that are other elements. This means that there are electrical connections between the carrier 1026 (may be a printed circuit board (PCB)) and the additional electronic devices. The structure of the heart rate monitoring device according to the present embodiment can be applied not only to the device for measuring the heart rate but also to devices for measuring a pulse wave and a pulse.

Fifth Embodiment

A heart rate monitoring device 1050 as a biological information measuring device according to a fifth embodiment will be described with reference to FIG. 16. FIG. 16 is a front view showing a heart rate monitoring device as the biological information measuring device according to the fifth embodiment. Although not shown in FIG. 16, the heart rate monitoring device 1050 as the biological information measuring device according to the fifth embodiment is worn on the arm of the user using a fixing unit, such as a band, as in the first embodiment described above.

The heart rate monitoring device 1050 as the biological information measuring device according to the fifth embodiment includes the additional electronic devices (for example, a processor 1052 and a driver 1054) described above. External electrical connection terminals (not shown) are not disposed on the same carrier 1026 as the sensor elements (the light emitting element 1221 as a light emitting portion and the light receiving element 1222 as a light receiving portion). That is, the additional electronic devices are disposed on a separate carrier or substrate from the sensor elements. Through such a configuration, a required additional electronic device can be mounted in the heart rate monitoring device 1050 while maintaining good contact between the skin and the sensor elements (the light emitting element 1221 and the light receiving element 1222). For example, an external electrical connection terminal can be disposed on the side surface of the carrier 1026.

As described above, different types of sensors can be used in the biological information measuring device according to the invention. For example, when the light receiving element 1222 is an electrical sensor, two skin conductance electrodes (for example, sensor elements (the light emitting element 1221, the light receiving element 1222 shown in FIG. 13)) that are in contact with the skin of the user to measure the conductivity of the user are covered with the skin. Furthermore, two or more types of sensors can be used in this kind of biological information measuring device, and the number of sensor elements does not matter.

Figure 17:
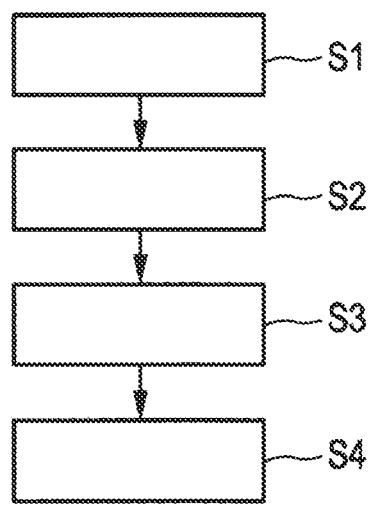
FIG. 17 is a flowchart of a method of manufacturing the biological information measuring devices according to the second to fifth embodiments.

In the second to fifth embodiments, a flowchart of a method of manufacturing the proposed biological information measuring device for measuring the physiological parameters is shown in FIG. 17.

In first step S1, the sensor 1022 configured to include at least two sensor elements (the light emitting element 1221 and the light receiving element 1222) for detecting a sensor signal is disposed on the carrier 1026. In second step S2, an electrical contact of the above sensor elements is formed on the carrier 1026. In third step S3, one or more frames 1041 and 1042 are formed on the carrier 1026 in the vicinity of the sensor 1022 and/or the separate sensor elements (the light emitting element 1221 and the light receiving element 1222). In fourth step S4, the insulating material 1032 is injected into regions surrounded by the frames 1041 and 1042, which do not cover the upper surfaces 1221a and 1222a of the sensor elements (the light emitting element 1221 and the light receiving element 1222) provided on the carrier 1026. As a result, the regions are filled with the insulating material 1032.

According to the second to fifth embodiments described above, a method of protecting of the electrical contact that does not have an adverse effect on the performance of the biological information measuring device is proposed. In addition, each sensor is formed in a method of maintaining the performance of the sensor. For example, at least one of the frames 1041 and 1043 prevents the shift of the sensor position with respect to the skin. In addition, at least one of the frames 1041 and 1043 can help to prevent the emitted direct light from being incident on the light receiving element 1222. Preferably, the heights of the frames 1041 and 1043 around the light emitting elements 1221 and 1223 on a side that the light receiving element 1222 faces should be smaller than the heights of the upper surfaces 1221a and 1223a of the light emitting elements 1221 and 1223. In addition, the surrounding frame 1042 around the light receiving element 1222 may be higher than the upper surface 1222a of the light receiving element 1222.

Also in the biological information measuring device according to the second to fifth embodiments described above, it is possible to apply the configuration based on the gap between the light emitting portion and the light receiving portion that has been described in the first embodiment. By adopting such a configuration, the same effect as in the first embodiment can be obtained.

Sixth Embodiment

The biological information measuring device of the first to fifth embodiments described above may include various sensors, such as a strainmeter, a thermometer, an acceleration sensor, a gyro sensor, a piezoelectric sensor, an air pressure sensor, a sphygmomanometer, an electrochemical sensor, a global positioning system (GPS), and a vibration meter. By providing these sensors, it is possible to derive information regarding the physiological state of an individual based on data indicating one or more physiological parameters, such as a heart rate, a pulse, a variation between beats, elektrokardiogram (EKG), electrocardiogram (ECG), a respiratory rate, skin temperature, body temperature, heat flow of the body, galvanic skin response, galvanic skin reflex (GSR), electromyogram (EMG), electroencephalogram (EEG), electrooculography (EOG), blood pressure, body fat, a hydration level, an activity level, body motion, oxygen consumption, glucose, a blood sugar level, a muscle mass, pressure applied to the muscle, pressure applied to the bone, ultraviolet absorption, a sleep state, physical condition, a stress state, and a posture (for example, recumbent, upright, and sitting). In addition, values obtained by these various sensors may be transmitted to portable communication terminals, such as a smartphone, a mobile phone, and a feature phone, or to information processing terminals, such as a computer and a tablet computer, and calculation processing of physiological parameters may be executed by the portable communication terminals or the information processing terminals.

The user inputs the profile of the user to the biological information measuring device, the portable communication terminal, or the information processing terminal before measuring the biological information. Therefore, in order to maximize the possibility of establishing and maintaining the healthy life style recommended based on the profile and the biological information measurement result, the user can receive the unique characteristic information and environmental information of the user that need to be addressed. As provided information, one or a plurality of items of exercise information such as an exercise type, exercise intensity, and exercise time, meal information such as meal time, the amount of food, recommended intake food or intake menu, intake food or intake menu that should be avoided, life assistance information such as sleeping time, depth of sleep, quality of sleep, wake-up time, time for the office, working hours, stress information, calorie consumption, calorie intake, and calorie balance, physical information such as basal metabolism, body fat mass, body fat percentage, and muscle mass, dosing information, supplements intake information, and medical information can be mentioned.

As examples of the profile of the user that is input in advance, it is possible to mention one or more of age, date of birth, sex, hobby, occupation, blood type, past sports history, activity level, diet, regularity of sleep, regularity of bowel habits, situation adaptability, persistence, responsiveness, strength of reaction, character of the user such as a nature, independence level of the user, independence formation, self-management, sociability, memory and academic fulfillment capability, arousal level of the user, perceptual speed, capability of avoiding attention alienation factor, attention of the user including arousal and self-supervision capability, attention-sustaining capability, weight, height, blood pressure, health state of the user, medical examination results of a doctor, day to meet a doctor, presence or absence of contact with a doctor or a health administrator, drugs and supplements being taken currently, allergies, history of allergy, current allergy symptoms, findings of behavior related to health, disease history of the user, surgical history of the user, family history, social events such as divorce or unemployment that needs to be adjusted by the individual, beliefs about the health priorities of the user, values, capability to change behavior, events believed to cause stresses of life, stress management method, self-consciousness level of the user, empathy degree of the user, empowerment degree of the user, self-respect of the user, exercise of the user, sleep state, relaxation state, current routine of daily activities, character of an important person (for example, a spouse, a friend, a coworker, or a boss) in the life of the user, and perception of the user about whether or not there is a collision that inhibits the healthy lifestyle or causes stress in the relationship with the important person.

Figure 18:
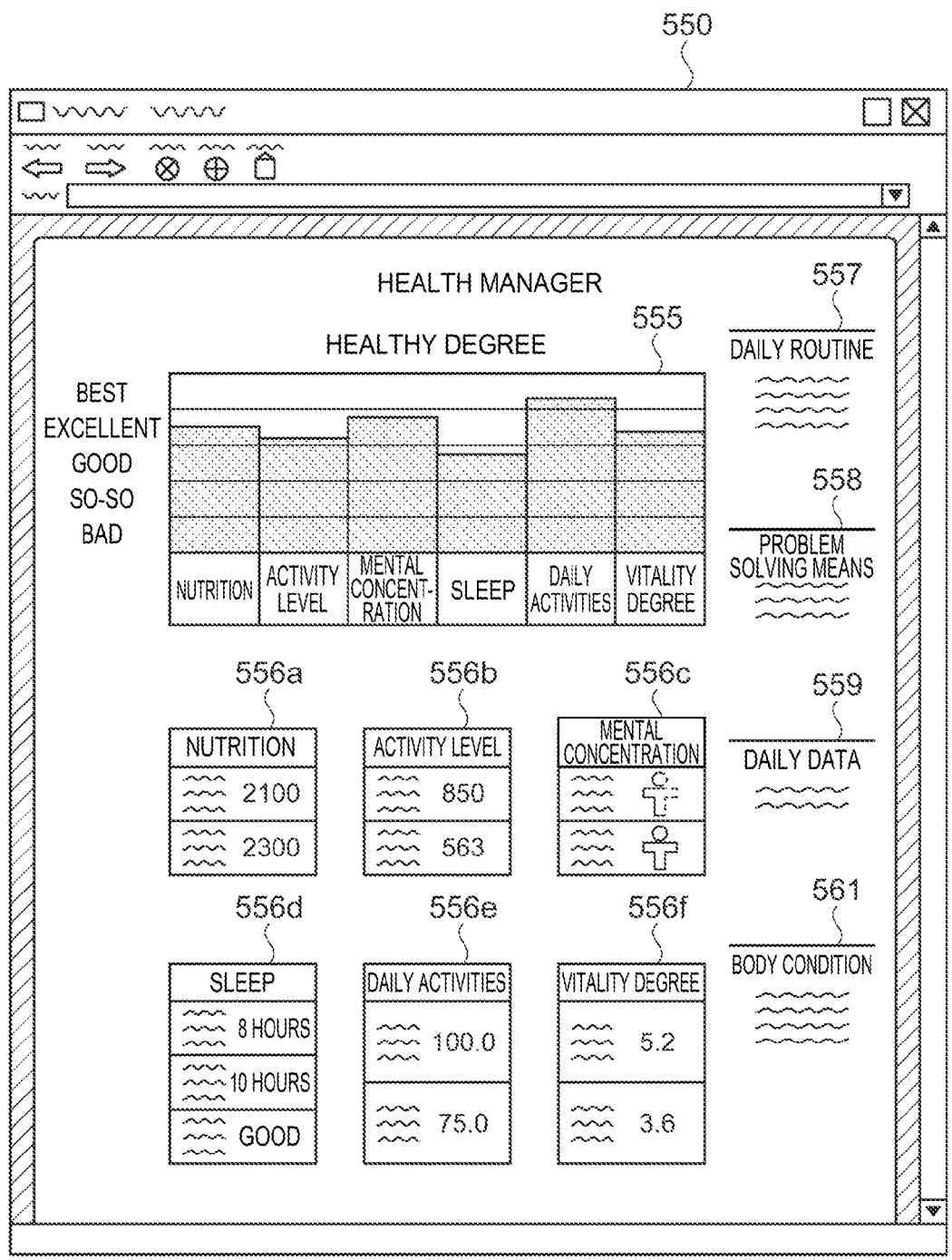
FIG. 18 is a diagram showing the outline of a web page that is the head page of a health manager in a biological information measuring device of a sixth embodiment.
Figure 19:
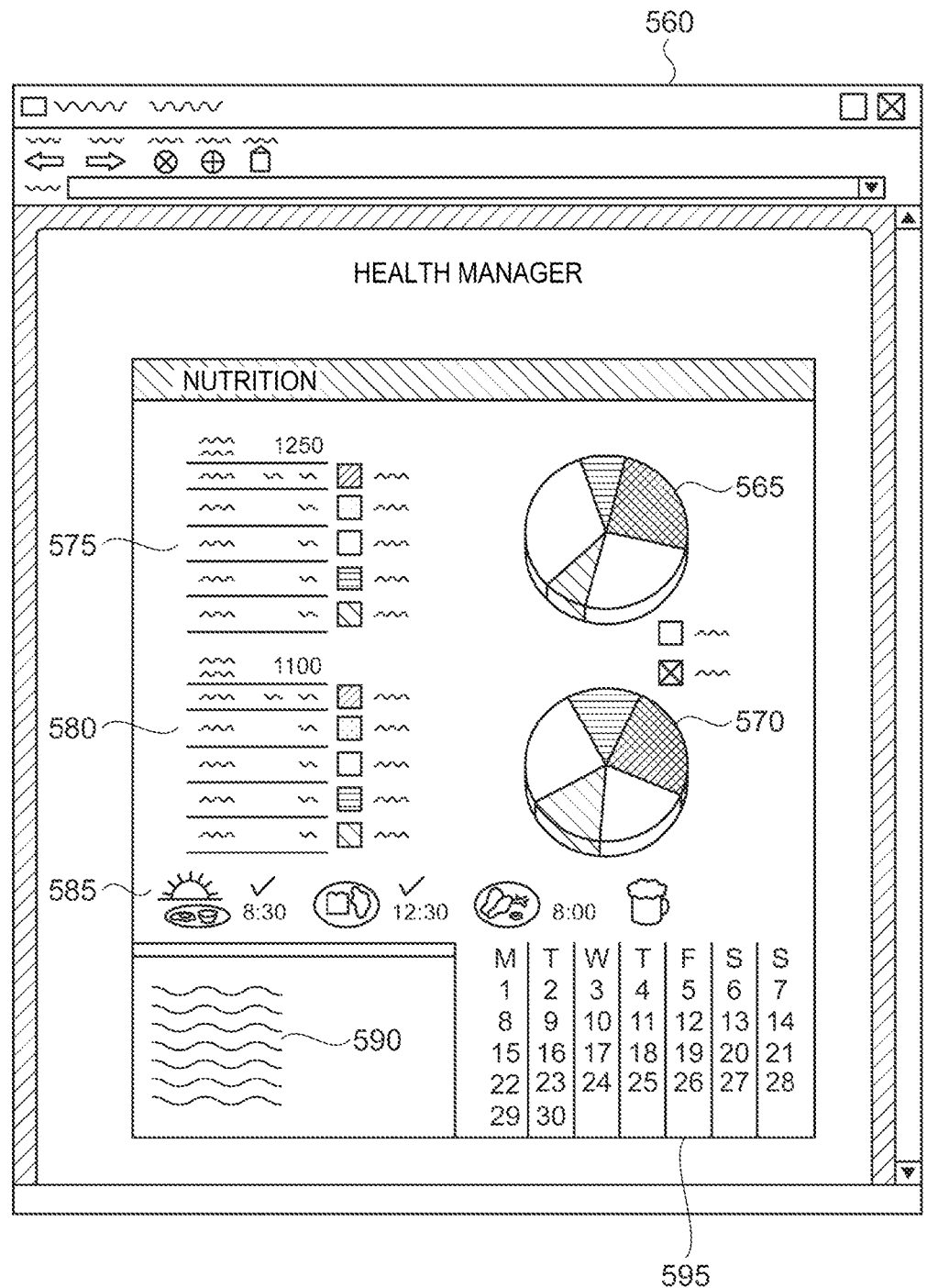
FIG. 19 is a diagram showing an example of a nutrition web page.
Figure 20:
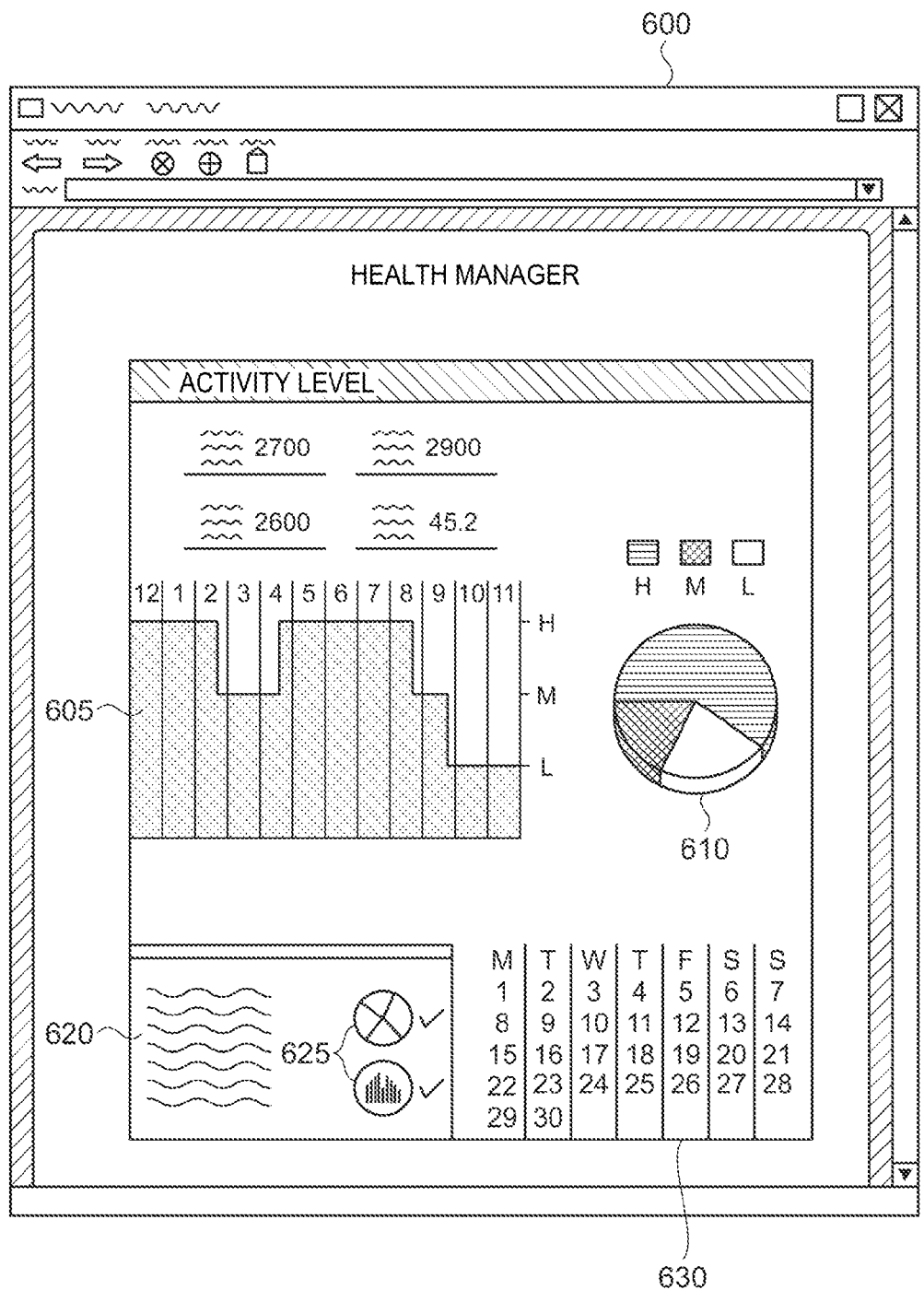
FIG. 20 is a diagram showing an example of an activity level web page.
Figure 22:
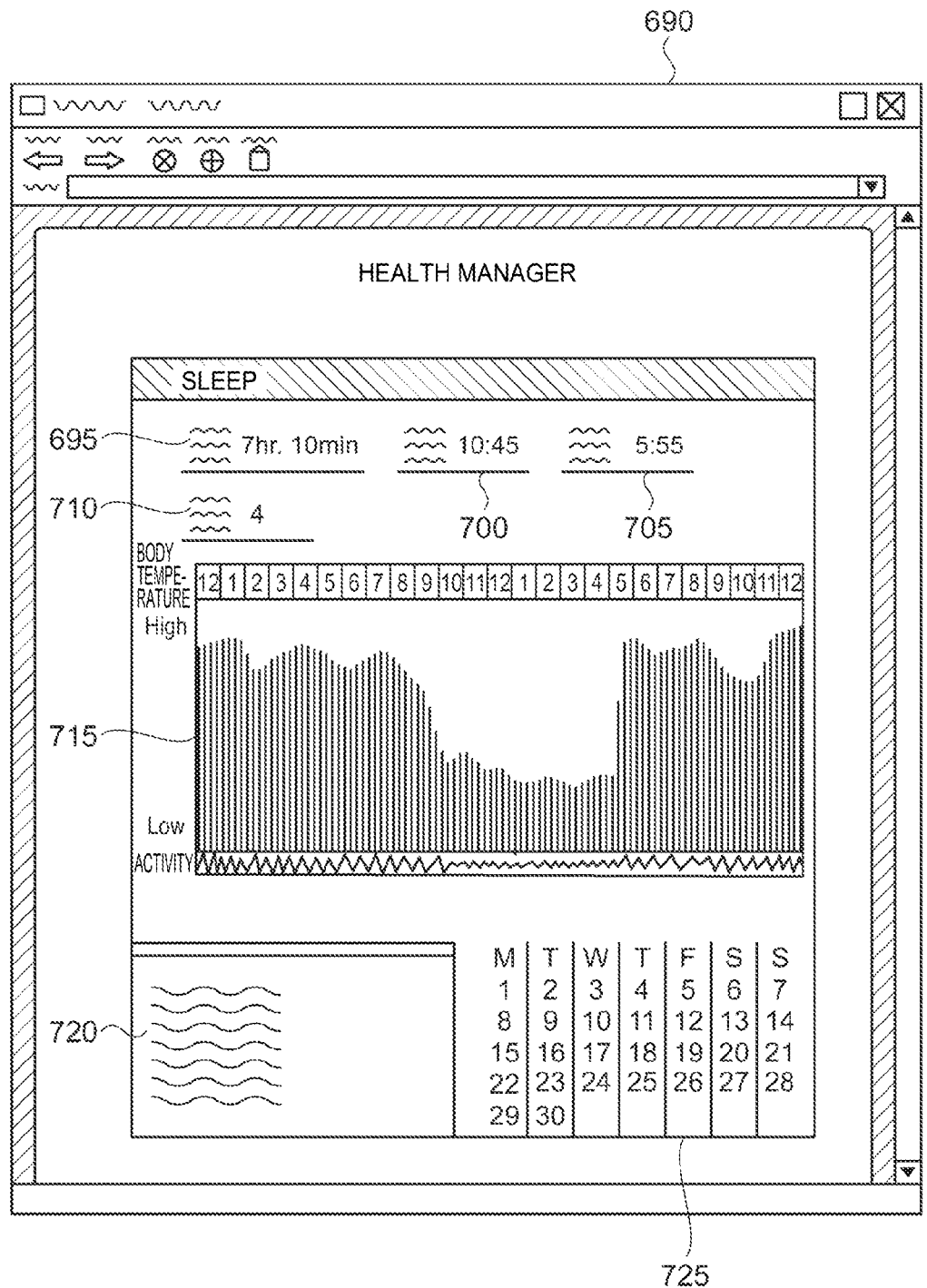
FIG. 22 is a diagram showing an example of a sleep web page.
Figure 23:
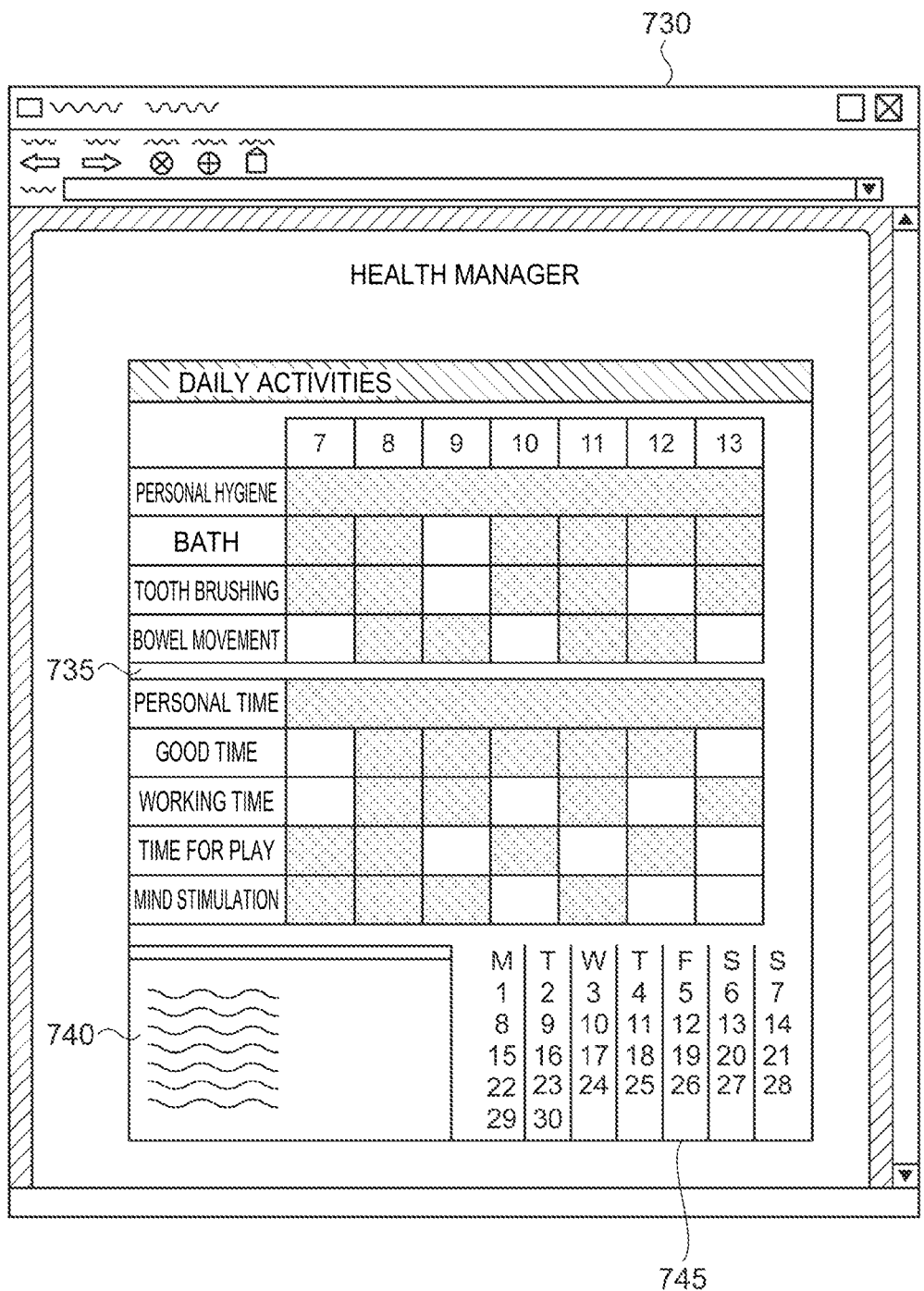
FIG. 23 is a diagram showing an example of a daily activity web page.
Figure 24:
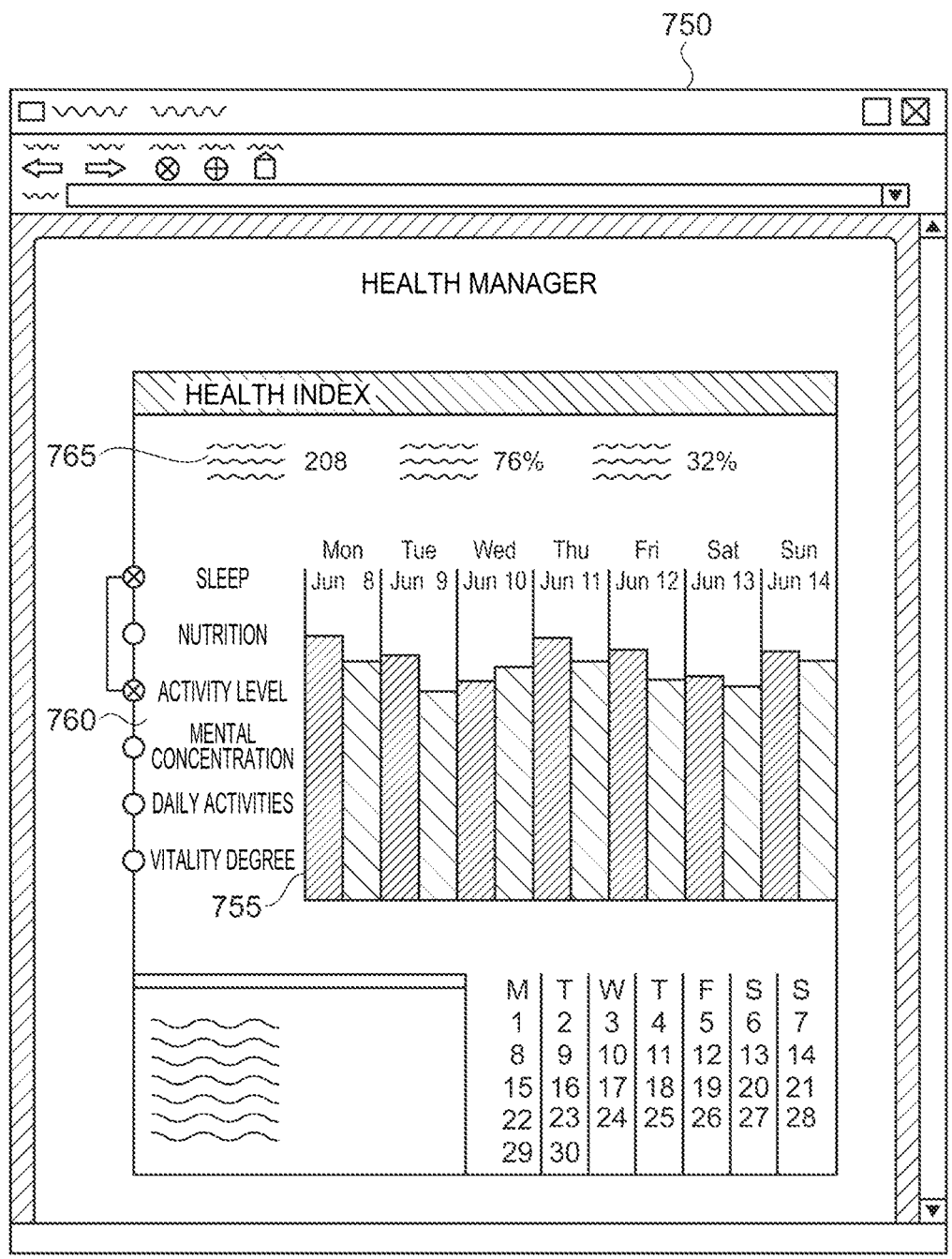
FIG. 24 is a diagram showing an example of a healthy degree web page.

A biological information measuring device according to a sixth embodiment that can receive the unique characteristic information and environmental information of the user that need to be addressed in order to maximize the possibility of establishing and maintaining the recommended healthy life style will be described with reference to FIGS. 18 to 24. FIG. 18 is a diagram showing the outline of a web page that is the head page of the health manager in the biological information measuring device of the sixth embodiment. FIG. 19 is a diagram showing an example of a nutrition web page, and FIG. 20 is a diagram showing an example of an activity level web page. FIG. 18 is a diagram showing an example of a mental concentration web page, and FIG. 22 is a diagram showing an example of a sleep web page. FIG. 23 is a diagram showing an example of a daily activity web page, and FIG. 24 is a diagram showing an example of a healthy degree web page.

Although not shown, the biological information measuring device according to the sixth embodiment includes a sensor device connected to a microprocessor, for example. In the biological information measuring device according to the sixth embodiment, data regarding various life activities, which is finally transmitted to a monitor unit and stored, or personal data or life information, which is input by the user through a web site maintained by the monitor unit, is processed by the microprocessor, and is provided as biological information. Hereinafter, a specific example will be shown and described.

A user accesses the health manager for the user through the web page, application software, and other communication media. FIG. 18 shows a web page 550, which is the head page of the health manager, as an example. In the web page 550 of the health manager shown in FIG. 18, various kinds of data are provided to the user. Data provided as described above includes, for example, one or more of (1) data indicating various physiological parameters based on values measured by various sensor devices, (2) data derived from the data indicating various physiological parameters, and (3) data indicating various context parameters generated by sensor devices or data input by the user.

Analysis state data is characterized in that a specific utility or algorithm is used to perform conversion to the healthy degree, which is obtained by calculation based on one or more of (1) data indicating various physiological parameters acquired by sensor devices, (2) data derived from the various physiological parameters, and (3) data indicating various context parameters acquired by sensor devices or data input by the user and conversion to (4) health and life style indices or the like. For example, based on the data input by the user in association with the ingested food and drink, it is possible to calculate calories, protein, fats, carbohydrates, and the amount of specific vitamins. As another example, by using the skin temperature, heart rate, respiratory rate, heat flow, and/or GSR, it is possible to provide the user with the index of the stress level over a desired period of time. As still another example, by using the skin temperature, heat flow, variation between beats, heart rate, respiratory rate, heat flow, body center temperature, galvanic skin response, EMG, EEG, EOG, blood pressure, oxygen consumption, ambient sound, and body motion detected by a device such as an accelerometer, it is possible to provide the user with the index of the sleep pattern over a desired period of time.

A health indicator 555 as a healthy degree is displayed on the web page 550 shown in FIG. 18. The health indicator 555 is a graphical utility for measuring the record of the user and the degree of achievement of the recommended healthy daily routine and feeding back them to the member user. Thus, the health indicator 555 shows the progress of the action on the health state or health maintenance to the member user. The health indicator 555 includes six categories regarding the health and life style of the user, that is, nutrition, activity level, mental concentration, sleep, daily activities, and vitality degree (overall impression). The category of "nutrition" relates to information regarding which, when, and how much the person (user) ate and drank. The category of "activity level" relates to the amount of movement indicating how much the person moved around. The category of "mental concentration" relates to the quality (capacity) of the activity for becoming in a relaxation state from the highly concentrated state of the person (user) and a time for which the person concentrates on the activity. The category of "sleep" relates to the quality and amount of sleep of the person (user). The category of "daily activities" relates to activities, which should be done by the person (user), and the healthy risk that the person has. The category of "vitality degree (impression)" relates to a common perception method regarding whether the user feels good or bad on a specific day. Preferably, each category has a level display or a bar graph showing which record the user has achieved regarding the category on a scale that changes between "bad" and "good".

When the first examination described above has been ended for each member user, a profile to provide a summary of the characteristics of the user and the living environment is created, and a recommended healthy daily routine and/or target are presented to the user. The recommended healthy daily routine includes an arbitrary combination of specific advice on appropriate nutrition, exercise, mental concentration, and daily activities (life) of the user. As a guide regarding how to include the activity related to the recommended healthy daily routine in the life of the user, an exemplary schedule or the like may be presented. The user takes the examination periodically, and practices the above-described items based on the result.

The category of "nutrition" is calculated from both the data input by the user and the data detected by the sensor device. The data input by the user includes breakfast, lunch, dinner, any snack time or dining time, food and drink to eat and drink, supplements such as vitamins, and water or other liquids to drink during the time selected in advance (drinking water or liquid food). Based on such data or stored data regarding the known properties of a variety of food, a central monitoring unit calculates known nutritional values, such as calories or the content of proteins, fats, carbohydrates, and vitamins.

In the category of "nutrition", it is possible to determine a recommended healthy daily routine based on the bar graph showing the nutrition of the health indicator 555. The recommended healthy daily routine can be adjusted based on information, such as sex, age, and height/weight of the user. The amount of calories, water, or nutrients taken every day, such as proteins, fibers, fats, and carbohydrates, and the target percentage of a specific nutrition with respect to the total intake can be set by the user or the representative on behalf of the user. Meal times of one day, the consumption of water of one day, and the type and amount of food to be eaten every day, which are input by the user, are included in parameters used to calculate the bar graph.

The nutritional information is presented to the user through a nutrition web page 560 shown in FIG. 19. Preferably, the nutrition web page 560 includes nutrition value charts 565 and 570, which show the actual and target values of nutrition in a pie chart, and nutrition charts 575 and 580, which show the actual total amount of nutrition and the target total amount of nutrition. It is preferable that the nutrition value charts 565 and 570 show items, such as carbohydrates, proteins, and fats, by percentage, and it is preferable that the nutrition charts 575 and 580 show the total value and the target value of calories with divided components, such as fats, carbohydrates, proteins, and vitamins. The web page 560 also includes history 585 indicating the time at which food and water were consumed, a hyperlink 590 allowing the user to directly check news articles relevant to nutrition, advice to improve the daily routine on nutrition, and relevant advertisements on the network, and a calendar 595 by which an applied period can be selected. Items shown in the hyperlink 590 can be selected based on the information obtained from the individual by examination and the record of the individual measured by the health indicator.

The category of "activity level" of the health indicator 555 is designed to assist the checking of the user regarding when and how the user worked (moved) on the day, and both the data input by the user and the data detected by the sensor device can be used. For example, details of the daily activities of the user, such as "user works on the desk from 8:00 a.m. to 5:00 p.m. and then receives aerobics training from 6:00 p.m. to 7:00 p.m.", are included in the data input by the user. The relevant data detected by the sensor device includes a heart rate, exercise detected by a device such as an accelerometer, heat flow, respiratory rate, amount of consumed calories, GSR, and hydration level, and these can be acquired by the sensor device or the central monitoring unit. The amount of consumed calories can be calculated by various methods, such as multiplication of the type of exercise input by the user and the duration of the exercise input by the user, multiplication of the detected exercise and exercise time and the filter constant, or multiplication of the detected heat flow and time and the filter constant.

In the category of "activity level", it is possible to determine a recommended healthy daily routine based on the bar graph showing the activity level of the health indicator 555. The recommended healthy daily routine is minimum target calories consumed in the activities. In addition, the minimum target calories can be set based on information, such as sex, age, height, and weight of the user. Parameters used in the calculation of the bar graph include a time spent for various kinds of exercise or vigorous life style activities, which is input by the user and/or is detected by the sensor device, or calories burned above the energy consumption parameter calculated in advance.

The information regarding the activities (movement) of the individual user is presented to the user through an activity level web page 600 shown in FIG. 20. The activity level web page 600 includes an activity graph 605 in the form of a bar graph to monitor the activities of the user using three categories, that is, monitor the activities of the user with "high", "medium", and "low" for a predetermined unit time. An activity percentage chart 610 of the pie chart form can be presented to show the percentage of a predetermined period, such as one day, spent in each category by the user. In addition, a calorie display (not shown) for displaying items, such as the total amount of burned calories, the target value of daily burned calories, the total value of calorie intake, and aerobics exercise time, can also be provided on the activity level web page 600. The activity level web page 600 includes at least one hyperlink 620 in order that the user can directly check the relevant news articles, advice to improve the daily routine on the activity level, and relevant advertisements on the network.

Although the activity level web page 600 can be viewed in various formats, it is possible to make a graph or a chart such as a bar graph, a pie chart, or both thereof selectable by the user. The bar graph or the pie chart can be selected by an activity level check box 625. An activity level calendar 630 is provided in order to be able to select an application period or the like. The item shown in the hyperlink 620 can be selected based on the information extracted from the individual by examination and the record measured by the health indicator.

The category of "mental concentration" of the health indicator 555 is designed to assist the user in monitoring the parameter regarding a time for which the user performs activities for making the body reach a deep relaxation state while concentrating the mind, and is based on both the data input by the user and the data detected by the sensor device. Specifically, the user can input the start and end times of relaxation activities, such as yoga or meditation. The quality of these activities determined by the depth of mental concentration can be measured by monitoring the parameters including the skin temperature, heart rate, respiratory rate, and heat flow that are detected by the sensor device. It is also possible to use the percentage change in GSR obtained by either the sensor device or the central monitoring unit.

In the category of "mental concentration", the recommended healthy daily routine can be determined based on the bar graph showing the activity level of the mental concentration of the health indicator 555. The recommended healthy daily routine is displayed including a daily participation into the activities to deeply relax the body in a highly concentration state of the spirit. The skin temperature, the heart rate, the respiratory rate, and the heat flow detected by the sensor device and the percentage change in GSR from the baseline indicating the length of the time spent for mental concentration activities and the depth or quality of mental concentration activities are included in the parameters used in the calculation of the bar graph.

Figure 21:
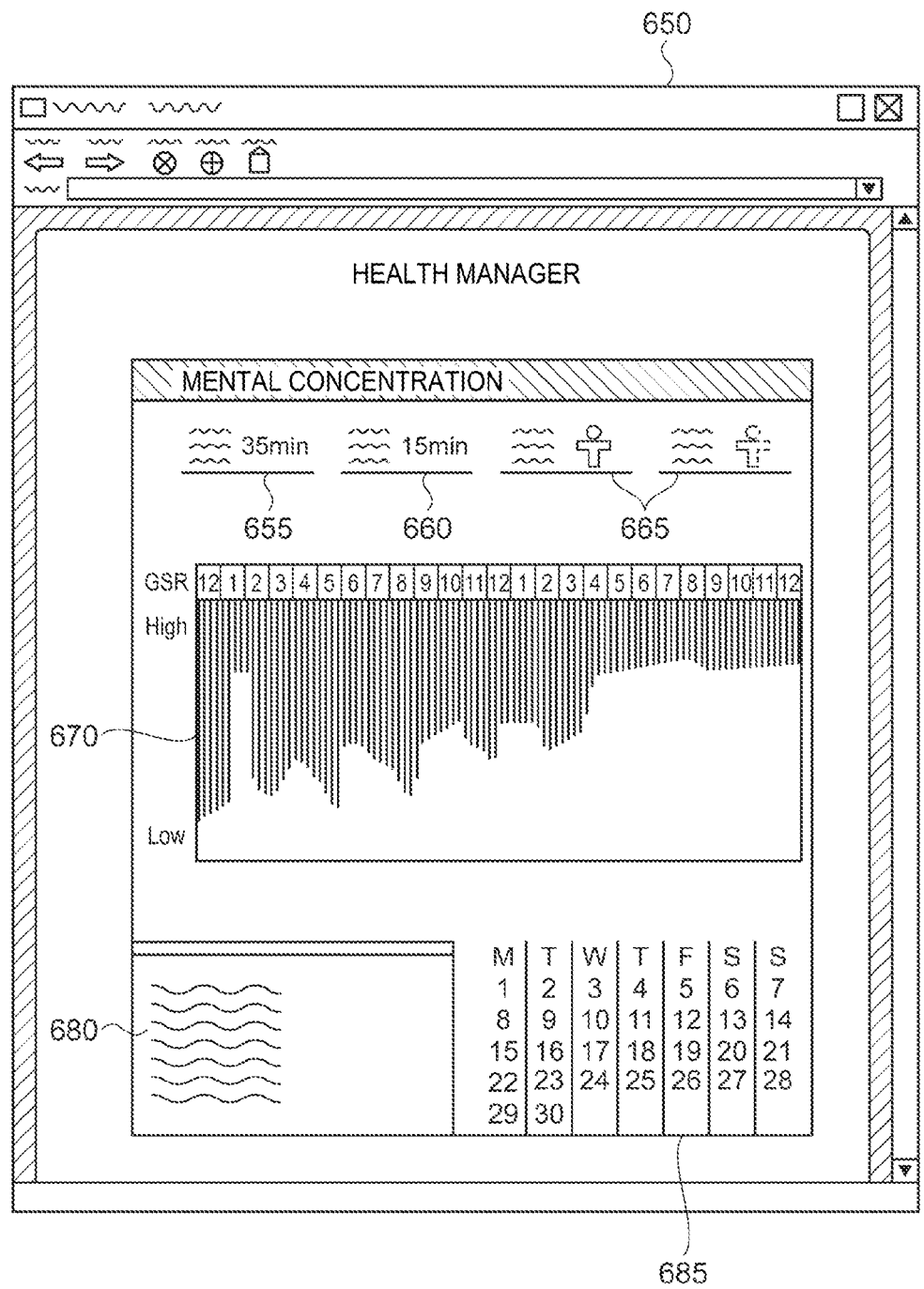
FIG. 21 is a diagram showing an example of a mental concentration web page.

The information regarding the time spent for the activity to look back upon himself or herself (introspection) and the mental concentration activities to deeply relax the body is presented to the user through a mental concentration web page 650 shown in FIG. 21. In addition, the mental concentration activities may be called a session. The mental concentration web page 650 includes a time spent in session 655, a target time 660, and a comparison portion 665 indicating the target value and the actual value of the depth of mental concentration, and a histogram 670 indicating the overall stress level derived from the skin temperature, heart rate, respiratory rate, heat flow, and/or GSR.

In the comparison portion 665, the human outline indicating the mental concentration state as a target is shown by the solid line, and the human outline indicating the actual mental concentration state is changed between a state that is blurred depending on the level of mental concentration (shown by the broken line in FIG. 21) and the solid line. The preferable mental concentration web page 650 includes a hyperlink 680 allowing the user to directly check the relevant news articles, advice to improve the daily routine on the mental concentration, and relevant advertisements on the network and a calendar 685 allowing the user to select the advice to improve the daily routine on the mental concentration, relevant advertisements, and application period. Items shown in the hyperlink 680 can be selected based on the information obtained from the individual by examination and the record measured by the health indicator.

The category of "sleep" of the health indicator 555 is designed to be able to assist the user in monitoring the sleep pattern and the quality of sleep. This category is intended to help the user learn the importance of sleep in a healthy life style and the relationship between the sleep and the circadian rhythm that is a daily normal change in the function of the body. The category of "sleep" is based on both the data input by the user and the data detected by the sensor device. The bedtime and wake-up time (sleeping time) and the rank of the quality of sleep are included in the data that the user inputs between the relevant time intervals. Skin temperature (body temperature), a heat flow, a variation between beats, a heart rate, a pulse rate, a respiratory rate, body center temperature, galvanic skin response, EMG, EEG, EOG, blood pressure, and oxygen consumption are included in the relevant data obtained from the sensor devices. In addition, ambient sound and body motion detected by a device, such as an accelerometer, are also included in the relevant data. Then, using these pieces of data, it is possible to calculate and derive the bedtime and the wake-up time, sleep interruption and the quality of sleep, the depth of sleep, and the like.

The bar graph showing the sleep of the health indicator 555 is displayed for a healthy daily routine including the securing of the preferred minimum sleeping time at every night, predictable bedtime, and wake-up time. Daily bedtime and wake-up time that are detected by the sensor device or are input by the user and the quality of sleep, which is ranked by the user or is derived from other pieces of data, are included in the specific parameters that enable the calculation of the bar graph.

The information regarding sleep is presented to the user through a sleep web page 690 shown in FIG. 22. The sleep web page 690 includes a sleeping time display 695 based on either the data from the sensor device or the data input by the user, a user bedtime display 700, and a user wake-up time display 705. The quality of sleep input by the user can also be displayed using a sleep quality rank 710. When performing the display exceeding the time interval of the day in the sleep web page 690, the sleeping time display 695 can be displayed as a total value, and the bedtime display 700, the wake-up time display 705, and the sleep quality rank 710 can be calculated and displayed as an average value. The sleep web page 690 also includes a sleep graph 715 that can be selected by the user who calculates and displays one sleep-related parameter for a predetermined time interval. FIG. 22 shows a change in the heat flow (body temperature) in one day. This heat flow tends to be low during sleep and high at the time of wake-up. From this information, it is possible to obtain the biorhythm of the person.

Through the sleep graph 715, data from the accelerometer built into the sensor device to monitor the movement of the body is graphically displayed. The sleep web page 690 can include a hyperlink 720 allowing the user to directly check the news articles related to sleep, advice to improve the daily routine on sleep, and relevant advertisements on the network and a sleep calendar 725 for selecting the relevant time interval. Items shown in the hyperlink 720 can be specially selected based on the information obtained from the individual by examination and the record measured by the health indicator.

The category of "daily activities" of the health indicator 555 is designed to be able to assist the user in monitoring the specific activities and risk related to health or safety, and is based on the data input by the user. The category of "daily activities" on the activities of daily life includes four categories of subordinate concepts. Specifically, the category of "daily activities" on the activities of daily life is divided into (1) item related to personal hygiene to enable the user to monitor the activities, such as brushing teeth using a toothbrush or a floss or taking a shower, (2) item related to health maintenance to track whether or not the user takes medicine or supplements according to a prescription and to enable the user to monitor the consumption of tobacco or alcohol, (3) item related to personal time to enable the user to monitor the time to spend with his or her family or friends or leisure and mental concentration activities, and (4) item related to responsibility to enable the user to monitor household chores, household activities, and the like.

In the category of "daily activities", it is preferable to display the recommended healthy daily routine, which will be described below, through the bar graph showing "daily activities" of the health indicator 555. As an example of the daily routine on personal hygiene, it is preferable that the user takes a shower or takes a bath every day, keeps the teeth clean every day using a toothbrush and floss, and maintains a regular bowel movement. As an example of the daily routine on health maintenance, it is preferable that the user takes medicine, vitamins, and/or supplements, stops smoking, is moderate in drink, and monitors the health every day using the healthy manager. As an example of the daily routine on personal time, it is preferable that the user creates at least a predetermined time to spend with his or her family every day, spends a good time with friends, reduces a working time, prepares a time for leisure or play, and performs activities using the head. As an example of the daily routine on responsibility, it is preferable that the user performs household chores, is not late for work, and keeps promises. The bar graph is determined by the information input by the user, and/or is calculated based on the degree that the user completes the listed activities every day.

The information regarding the activities is presented to the user through a daily activity web page 730 shown in FIG. 23. An activity chart 735 in the daily activity web page 730 shows whether or not the user has performed the activities required by the daily routine. In the activity chart 735, one or more of the subordinate concepts can be selected. In the activity chart 735, a box with a color or shade indicates that the user has performed the required activity, and a box with no color or shade indicates that the user has not performed the activity. The activity chart 735 can be viewed by being created in a selectable time interval. FIG. 23 shows the categories of personal hygiene and personal time in a specific week as an example. The daily activity web page 730 can include a hyperlink 740 allowing the user to directly check the relevant news articles, advice to improve the daily routine on the activities of daily life, and relevant advertisements on the network and a daily activity calendar 745 for selecting the relevant time interval. Items shown in the hyperlink 740 can be selected based on the information obtained from the individual by examination and the record measured by the health indicator.

The category of "vitality degree" of the health indicator 555 is designed so that the user can monitor the recognition regarding whether or not the user is vital on a specific day, and is based on the essentially subjective grade information that is directly input by the user. The user determines the ranking for the following nine regions, that is, (1) mental acuity, (2) mental and psychological happiness level, (3) energy level, (4) ability to cope with life stress, (5) degree that values face-to-face, (6) physical happiness, (7) self-control, (8) motive, and (9) consolation by the relationship with others, preferably using a scale from 1 to 5. These degrees (grades) are averaged, and the result is used to calculate the bar graph of the health indicator 555.

FIG. 24 shows a web page 750 of the vitality degree. The web page 750 of the healthy degree allows the user to check the vitality degree over a selectable time interval including arbitrary continuous or discontinuous dates. In the example shown by FIG. 24, the healthy degree is displayed as a health index. In the web page 750 of the vitality degree, the user can make a selection to check a bar graph 755 of the vitality degree for one category by using a selection box 760 of the vitality degree, or the user can compare the bar graph 755 of the vitality degree for two or more categories. For example, in order to check whether or not the overall sleep grade has been improved compared with the previous month, the user may want to display only the bar graph of sleep. Alternatively, by displaying sleep and the activity level at the same time, the grade of sleep and the grade of the activity level corresponding thereto may be compared and evaluated to check whether or not there is any correlation between the respective dates. By displaying the grade of nutrition and the grade of vitality for a predetermined time interval, whether or not there is any correlation between daily diet habits, diet habits during the interval, and the vitality degree may be checked. As an example for explanation, FIG. 24 shows a comparison using the bar graph of sleep and activity level in the week of June 8 to June 14. In addition, the web page 750 of the vitality degree also includes a tracking calculator 765 to display access information, such as the total number of days for which the user has logged in to the health manager to use the health manager, the proportion of days for which the user has used the health manager since admission, and the proportion of days for which the user has used the sensor device in order to collect data, and the statistics.

An example of the web page 550 that is the head page of the health manager shown in FIG. 18 includes summaries 556a to 556f of a plurality of categories each of which corresponds to the category of the health indicator 555 as a vitality degree and which can be selected by the user. The summaries 556a to 556f of the respective categories present a subset of data after being selected in advance and being filtered for the corresponding category. The summary 556a of the nutrition category shows the daily target value and the daily actual value of calorie intake. The summary 556b of the activity level category shows the daily target value and the daily actual value of burned calories. The summary 556c of mental concentration shows the target value and the actual value of the depth of mental concentration. The summary 556d of the sleep category shows the target sleeping time, the actual sleeping time, and the grade of the quality of sleep. The summary 556e of the daily activity category shows the target score and the actual score based on the percentage of completed activities with respect to the recommended healthy daily routine (daily activities). The summary 556f of the category of the vitality degree shows the target grade and the actual grade of the vitality degree of the day.

The web page 550 can also include comments (not shown) to the user based on the hyperlink (not shown) to the news articles and the trend, such as malnutrition, checked by the first examination, and signs (not shown). It is also possible to include a daily routine portion 557 to provide the user with information every day. As the comments of the daily routine portion 557, for example, the intake of water required every day, the advice of specific means for enabling the same, and the like can be displayed. In addition, the web page 550 can include a problem solving section 558 to actively evaluate the record of the user in each category of the health indicator 555 and present the advice for improvements. For example, when it is indicated that the sleep level of the user is "low" and the user has insomnia according to the system, the problem solving section 558 can advise a method for improving sleep. In addition, the problem solving section 558 can include user question regarding improvements in the record. In addition, the web page 550 can include a daily data section 559 to start the input dialog box. Through the input dialog box, the user can easily input various kinds of data required by the health manager. As is known in the related art, the selection of a list presented in advance or the input of a normal free text format is possible for the input of data. In addition, the web page 550 can include a body state section 561 to give information regarding vital signs, such as the user's height, weight, body measurement values, BMI, heart rate, blood pressure, and arbitrary physiological parameters.

Modification Example of a Light Receiving Portion

Figure 25:
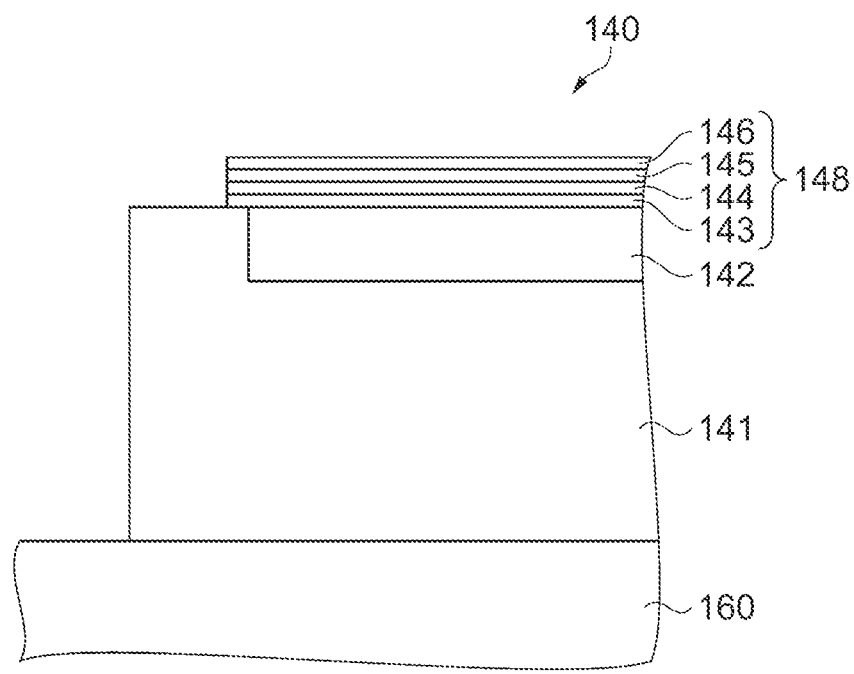
FIG. 25 is a partially sectional view showing a modification example of the light receiving portion.

Here, a modification example of the light receiving portion 140 will be described with reference to FIG. 25. FIG. 25 is a partially sectional view showing the modification example of the light receiving portion. As shown in FIG. 25, the light receiving portion 140 mounted on the substrate 160 (sensor substrate) can be realized by a PN-junction diode element 142 and the like formed on a semiconductor substrate 141. In this case, an angle limiting filter for narrowing down the light receiving angle or a wavelength limiting filter (optical filter film) 148 for limiting the wavelength of light incident on the light receiving element may be formed on the diode element 142. For example, the wavelength limiting filter (optical filter film) 148 can be configured to include a first oxide film 143, a first nitride film 144, a second oxide film 145, and a second nitride film 146 that are formed in order from the diode element 142 side. The modification example of the light receiving portion can also be applied to any of the embodiments described above.

By adopting such a configuration, the wavelength limiting filter (optical filter film) 148 can be provided in a smaller region. As a result, it is possible to provide a smaller biological information measuring module and a smaller biological information measuring device.

Modification Example of a Light Emitting Portion

Figure 26:
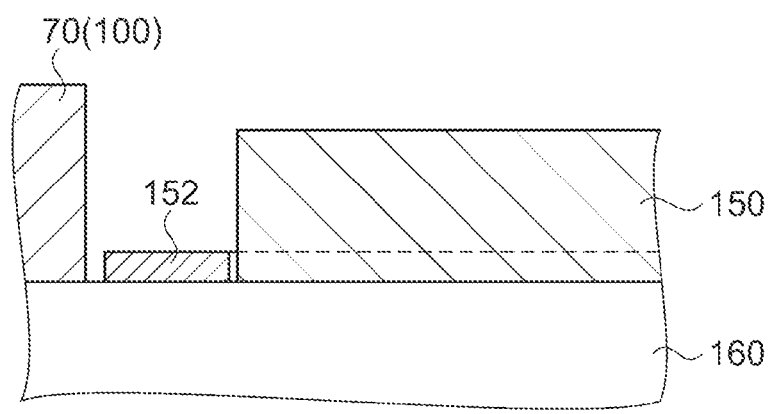
FIG. 26 is a partially sectional view showing a modification example of the light emitting portion.

Next, a modification example of the light emitting portion 150 will be described with reference to FIG. 26. FIG. 26 is a partially sectional view showing the modification example of the light emitting portion. As shown in FIG. 26, a wall portion 70 (100) and a reflective functional layer 152 for reflecting light emitted in the peripheral direction from the light emitting portion 150 are provided around the light emitting portion 150 mounted on the substrate 160 (sensor substrate). The reflective functional layer 152 may be provided so as to surround the entire periphery of the light emitting portion 150 or may be provided in at least a part of the periphery of the light emitting portion 150 in plan view seen from the upper surface side of the substrate 160. The modification example of the light emitting portion can also be applied to any of the embodiments described above.

By adopting such a configuration, light emitted in the peripheral direction of the light emitting portion 150 can be made to be reflected by the reflective functional layer 152, so that the light travels toward a measurement target. Therefore, since it is possible to increase the intensity (emission intensity) of light traveling toward the measurement target, it is possible to improve the measurement accuracy of biological information while ensuring stability.

While the above embodiments have been described in detail, it could be easily understood by those skilled in the art that various changes and modifications thereof could be made without departing from novel matters and effects of the invention. Therefore, such modification examples are intended to be included within the scope of the invention. For example, in this specification or the diagrams, a term that is described at least once together with different terms having a broader meaning or the same meaning can be replaced with the different terms in any parts of the specification or diagrams. The configurations and operations of the biological information measuring module, the light detection unit, the biological information measuring device, and the like are not limited to those described in the present embodiment, and various modifications can be made.

What is claimed is:

1. A biological information measuring module, comprising:
    a light receiving portion that receives light having passed through a target;
    a frame that surrounds the light receiving portion and that has a top surface that is configured to contact skin of a subject as the target; and
    a support portion that has a support surface and supports the light receiving portion and the frame on the support surface,
    wherein
        assuming that a width of the frame is L, a difference Δh between a height from the support surface to a top surface of the light receiving portion on an opposite side of the support surface and a height from the support surface to the top surface of the frame on an opposite side of the support surface is expressed by Expression (1):

$$\frac{5}{384} \times 0.016 \times L^4 \leq \Delta h \leq \frac{5}{384} \times 0.039 \times L^4, \quad (1)$$

and
    the difference Δh corresponds to a distance that extends from the top surface of the frame towards the support surface.

2. The biological information measuring module according to claim 1,
    wherein the difference Δh is expressed by Expression (2):

$$\frac{5}{384} \times 0.020 \times L^4 \leq \Delta h \leq \frac{5}{384} \times 0.025 \times L^4. \quad (2)$$

3. The biological information measuring module according to claim 2,
    wherein the width L is 3.0 mm≤L<4.5 mm.

4. A biological information measuring device comprising the biological information measuring module according to claim 3.

5. The biological information measuring module according to claim 2,
    wherein the width L is 4.0 mm≤L<4.5 mm.

6. A biological information measuring device comprising the biological information measuring module according to claim 5.

7. A biological information measuring device comprising the biological information measuring module according to claim 2.

8. The biological information measuring module according to claim 1, wherein
    the frame has a rectangular shape in a plan view, and
    the width L is a width of the frame in a short side direction of the rectangular shape.

9. A biological information measuring device comprising the biological information measuring module according to claim 8.

10. The biological information measuring module according to claim 1, wherein the height from the support surface to a top surface of the frame on the opposite side of the support surface is larger by Δh than the height from the support surface to the top surface of the light receiving portion on the opposite side of the support surface.

11. A biological information measuring device comprising the biological information measuring module according to claim 10.

12. The biological information measuring module according to claim 1, further comprising:
a light emitting portion that emits light to the target,
wherein the light emitting portion is supported on the support surface of the support portion.

13. The biological information measuring module according to claim 12,
wherein at least a part of the frame is disposed between the light receiving portion and the light emitting portion.

14. The biological information measuring module according to claim 13,
wherein the width L is a width of the frame in a direction in which the light receiving portion and the light emitting portion are connected to each other.

15. A biological information measuring device comprising the biological information measuring module according to claim 13.

16. A biological information measuring device comprising the biological information measuring module according to claim 12.

17. The biological information measuring module according to claim 1, further comprising:
a control unit,
wherein the support portion includes a connection terminal that electrically connects the light receiving portion and the control unit to each other.

18. The biological information measuring module according to claim 17,
wherein the support portion includes a through hole that connects the support surface and a back surface of the support portion to each other, the support surface and the back surface being front and back surfaces of the support portion, and
the connection terminal is provided on the back surface of the support portion so as to be connected to the through hole.

19. The biological information measuring module according to claim 17,
wherein a thickness of the support portion is larger than a thickness of a base portion of the control unit.

20. A biological information measuring device comprising the biological information measuring module according to claim 1.

* * * * *